(12) United States Patent
Corcoran

(10) Patent No.: US 8,609,080 B2
(45) Date of Patent: Dec. 17, 2013

(54) METHODS AND COMPOSITIONS FOR CONTROLLED RELEASE OF DRUGS

(75) Inventor: Robert C. Corcoran, Tie Siding, WY (US)

(73) Assignee: The University of Wyoming, Laramie, WY (US)

( * ) Notice: Subject to any disclaimer, the term of this patent is extended or adjusted under 35 U.S.C. 154(b) by 0 days.

(21) Appl. No.: 13/333,530

(22) Filed: Dec. 21, 2011

(65) Prior Publication Data

US 2012/0148521 A1    Jun. 14, 2012

Related U.S. Application Data

(63) Continuation of application No. 10/859,472, filed on Jun. 1, 2004, now Pat. No. 8,105,570, which is a continuation-in-part of application No. PCT/US02/40207, filed on Dec. 16, 2002.

(60) Provisional application No. 60/341,153, filed on Dec. 14, 2001.

(51) Int. Cl.
*A61K 31/74*    (2006.01)

(52) U.S. Cl.
USPC ..................................................... 424/78.29

(58) Field of Classification Search
USPC ..................................................... 424/78.29
See application file for complete search history.

(56) References Cited

U.S. PATENT DOCUMENTS

| | | |
|---|---|---|
| 4,346,709 A | 8/1982 | Schmitt |
| 4,386,026 A | 5/1983 | Ponpipom et al. |
| 4,489,056 A | 12/1984 | Himmelstein et al. |
| 4,842,868 A | 6/1989 | Helwing |
| 4,891,225 A | 1/1990 | Langer et al. |
| 5,017,693 A | 5/1991 | Hylarides et al. |
| 5,026,821 A | 6/1991 | Boustta et al. |
| 5,144,011 A | 9/1992 | Shen et al. |
| 5,216,115 A | 6/1993 | Kohn et al. |
| 5,258,453 A | 11/1993 | Kopecek et al. |
| 5,306,809 A | 4/1994 | Boon et al. |
| 5,316,774 A | 5/1994 | Eury et al. |
| 5,317,077 A | 5/1994 | Kohn et al. |
| 5,330,768 A | 7/1994 | Park et al. |
| 5,407,682 A | 4/1995 | Schacht et al. |
| 5,455,027 A | 10/1995 | Zalipsky et al. |
| 5,498,729 A | 3/1996 | Domb |
| 5,563,250 A | 10/1996 | Hylarides et al. |
| 5,654,381 A | 8/1997 | Hrkach et al. |
| 5,827,925 A | 10/1998 | Tremont et al. |
| 5,877,158 A | 3/1999 | Bosslet et al. |
| 5,955,068 A | 9/1999 | Gouin et al. |
| 5,962,686 A | 10/1999 | Ichihara et al. |
| 5,965,119 A | 10/1999 | Greenwald et al. |
| 6,214,966 B1 | 4/2001 | Harris |
| 6,251,430 B1 | 6/2001 | Zhang et al. |
| 6,274,175 B1 | 8/2001 | Gombotz et al. |
| 6,300,353 B1 | 10/2001 | Hayase et al. |
| 6,300,458 B1 | 10/2001 | Vandenberg |
| 6,303,148 B1 | 10/2001 | Hennink et al. |
| 6,359,111 B1 | 3/2002 | Meyer et al. |
| 2002/0064546 A1 | 5/2002 | Harris |

FOREIGN PATENT DOCUMENTS

| | | |
|---|---|---|
| WO | 9930727 | 6/1999 |
| WO | 9945008 | 9/1999 |

OTHER PUBLICATIONS

Wolff (Medicinal Chemistry) summarizes the state of the prodrug art (Wolff, Manfred E. "Burger's Medicinal Chemistry, 5ed, Part I", John Wiley & Sons, 1995, pp. 975-977).*
Banker et al, "Modern Pharmaceutics, 3ed.", Marcel Dekker, New York, 1996, pp. 451 and 596.*
Greene, T.W. and Wilts, P.G.M., "Protective Groups in Organic synthesis,".3rd Ed. (John Wiley & Sons, New York, 1999), Chapter 3, Protection for the Hydroxyl Group, pp. 17-292, Chapter 6, "Protection for the Thiol Group," pp. 454-493, and Chapter 7 "Protection for the Amino Group," pp. 494-653.
Carl, P., et al. A novel connector linkage applicable in prodrug design. Journal of Medicinal Chemistry. 1981, vol. 24, No. 5, pp. 479-480.
De Groot, F., et al. Elongated multiple electronic cascade and cyclization spacer systems in activatible anticancer prodrugs for enhanced drug release. Journal of Organic Chemistry. 2001, vol. 66, pp. 8815-8830.
Greenwald, R. et al. Drug delivery systems employing 1,4- or 1,6-Elimination: Poly(ethylene glycol) prodrugs of amine-containing compounds. Journal of Medicinal Chemistry. 1999, vol. 42, pp. 3657-3667.

(Continued)

*Primary Examiner* — Noble Jarrell
*Assistant Examiner* — Valerie Rodriguez-Garcia
(74) *Attorney, Agent, or Firm* — Ellen P. Winner; e winner & associates, pllc

(57) ABSTRACT

Methods and compositions for controlled release of amine, alcohol and thiol drugs, e.g., narcotic analgesics, and tricyclic amine antidepressants, are provided. The drug is releasably covalently bonded to a polymer or other activity-blocking moiety. Release is by an unmasking reaction resulting in the formation of a chemical group that undergoes a second reaction releasing the drug. For example, the narcotic analgesic fentanyl covalently attached to an inert polymer by way of its nitrogen through formation of a quaternary vinylammonium salt is released by hydrolysis of an acetal exposing an alcohol that undergoes an intramolecular nucleophilic substitution reaction involving displacement of the fentanyl nitrogen. Process rate is controlled by controlling the rate of the intramolecular substitution reaction through varying the number of atoms in the chain connecting the alcohol group and the vinylic carbon and/or by the addition of substituents on that chain, and/or by the acetal hydrolysis rate.

2 Claims, No Drawings

(56) References Cited

OTHER PUBLICATIONS

Lee, S., et al. Drug delivery systems employing 1,6-elimination: releasable poly(ethylene glycol) conjugates of proteins. Bioconjugate Chemistry. 2001, vol. 12, pp. 163-169.

Bogardus & Higuchi (1982) "Kinetics and Mechanism of Hydrolysis of Labile Quaternary Ammonium Derivatives of Tertiary Amines" J. Pharm. Sci, 71(7):729-735.

Ohwada, et al. (2002) "Synthesis of Novel Water Soluble Benzylazolium Prodrugs of Lipophilic Azole Antifungals" Bioorg Med Chem Lett 12(19):2775-2780.

* cited by examiner

METHODS AND COMPOSITIONS FOR CONTROLLED RELEASE OF DRUGS

CROSS-REFERENCE TO RELATED APPLICATIONS

This application is a continuation of U.S. application Ser. No. 10/859,472, filed Jun. 1, 2004, which is a continuation-in-part of PCT Application No. PCT/US02/40207 filed Dec. 16, 2002, which designates the United States and claims benefit of U.S. Provisional Application No. 60/341,153 filed Dec. 14, 2001, said applications being incorporated herein by reference to the extent not inconsistent herewith.

BACKGROUND OF THE INVENTION

There are many circumstances in which it is desirable to deliver drugs to an individual at a controlled rate, so as to extend the period of action of the drug over a convenient time span. The most common examples of this are decongestants and allergy medicines, in which it is very convenient for individuals to take a single pill every twelve hours, as opposed to having to take a pill every two to four hours. Another example is the use of timed-release formulations of pain relievers. Such formulations allow a convenient way for sufferers of chronic pain, such as arthritis or back pain, to lead more normal lives without the necessity of taking pills on a frequent basis. The lack of the necessity of taking pills on a frequent basis is of particular benefit because it may allow the individual to sleep through an entire night without pain or disturbance.

A number of means of achieving the controlled release of drugs have been utilized. Probably the most common means is to put coatings on small particles of the drug. When the drug is in the digestive tract, this coating gradually dissolves, releasing the drug. If one uses coatings of different thicknesses, or coatings have differing rates of dissolution, it is possible to deliver the drug at a number of different rates, thereby achieving a more steady physiological concentration over a long period of time. Multiple coatings may also be used, or coatings responsive to varying pH conditions in the body. Other methods besides coating drug particles have been used to achieve controlled release. These include embedding the drug in a polymer matrix or a vesicle, such as a liposome, which may be biodegradable, and relying on the diffusion of the drug from these matrices. By varying the polymer composition, the delivery rate may be varied.

Polymers used as drug delivery systems which release the drug upon biodegradation under appropriate conditions are disclosed in U.S. Pat. Nos. 6,274,175; 6,251,430; 5,955,068; 5,407,682; 5,330,768; 5,316,774; 5,026,821; 4,489,056; and 4,346,709; and U.S. patent publication US2002/0064546A1.

A number of patents disclose the use of cleavable conjugates of drugs with polymers or other molecules. Typically the bonds are easily hydrolyzable under mild conditions. See, e.g., U.S. Pat. Nos. 6,300,458; 6,214,966; 5,877,158; 5,827,925; 5,654,381; 5,563,250; 5,498,729; 5,455,027; 5,317,077; 5,306,809; 5,258,453; 5,216,115; 5,144,011; 5,017,693; 4,891,225; 4,842,868; and 4,386,026.

A significant problem in current controlled release technology for drugs is that it may be circumvented in a fairly straightforward fashion. This problem most frequently arises for analgesics. For example, there is currently a timed-release formulation of oxycodone (marketed under the trade name OXYCONTIN®) that is intended to provide for long-term pain relief when swallowed in a controlled release formulation. If the capsule or tablet is simply ground or chewed up thoroughly to destroy the microencapsulation around the drug, and then swallowed, all of the oxycodone is immediately available, and the individual receives a morphine-like "high." The fact that repeated use of high dosages of oxycodone may lead to addiction, coupled with the ease with which the controlled release mechanism of this drug may be circumvented, has unfortunately led to widespread abuse of the drug, to the point that there have been calls for its use to be banned or severely restricted.

While the purposeful circumvention of a timed-release mechanism is an obvious problem for narcotic analgesics, it may also become a problem for other drugs. In particular, there are drugs that have a relatively narrow window of safety—drugs for which the difference between an optimal dose and an overdose is not extremely large. Presentation of such drugs in a timed-release formulation that provides for their gradual delivery is an obvious solution to this problem; however, there exists the possibility of an accidental circumvention of the time-release process that can have disastrous consequences. In particular, there is an ever-increasing population of the elderly who take large numbers of a wide variety of pills, many of which have differing instructions for use. If a time-release formulation meant to be swallowed is mistaken for a type of tablet meant to be chewed, a potentially life-threatening dosage of drug may be rapidly delivered.

There is, therefore, a need for timed-release formulations for drugs allowing release to be precisely controlled, and a need for such formulations which are not easily circumventable.

All publications referred to herein are incorporated by reference to the extent not inconsistent herewith.

SUMMARY OF THE INVENTION

This invention relates to methods for the controlled release of drugs. In one embodiment, the drugs have been attached by means of a covalent bond to a polymer. The drugs are released in a two-stage process in which an unmasking reaction results in the formation of a chemical group that can then undergo a second reaction to release the drug. In a particular embodiment of this invention, the narcotic analgesic oxycodone is covalently attached to an inert polymer by way of its nitrogen through the formation of a quaternary vinylammonium salt, and then released by a sequence involving hydrolysis of an acetal that exposes an alcohol that may then undergo an intramolecular nucleophilic substitution reaction involving displacement of the nitrogen of oxycodone. The overall rate of this process may be controlled by either or both of the rates of the acetal hydrolysis (the unmasking reaction) or the intramolecular substitution reaction (the drug release reaction), but it is preferably controlled by the latter through varying the number of atoms in the chain connecting the alcohol group and a vinylic carbon, as well as by the addition of substituents on that chain. The rate may also be controlled by varying the nucleophilic atom involved in the intramolecular substitution reaction. Thus, in another particular embodiment of this invention, the narcotic analgesic fentanyl is covalently attached to an inert polymer by way of its nitrogen through the formation of a quaternary vinylammonium salt, and then released by a sequence involving hydrolysis of a carbamate that exposes an amine group that reacts in an intramolecular fashion involving displacement of the fentanyl nitrogen. This process occurs more rapidly than the corresponding intramolecular reaction involving an oxygen nucleophile.

The present invention provides methods and compositions that allow for the controllable release of a variety of drugs in a fashion that is difficult to purposefully circumvent. One embodiment of this invention comprises the following general elements: a polymeric support to which the drug is attached by way of a covalent chemical bond; a "triggering" functional group containing a triggering atom (also called a release-enhancing moiety) that is capable of accomplishing the rupture of the covalent chemical bond that attaches the drug to the polymer; and a "masking" group that serves to block the chemical reaction of the triggering group until it is removed by an "unmasking" reaction that exposes the triggering group in its chemically-reactive form.

The operation of one embodiment of the invention occurs in the following general fashion. The drug is attached to the polymer by means of a covalent bond that is not readily cleaved by the ordinary conditions found in the digestive tract (mouth, stomach, intestines). While attached to this polymer, the drug is not bioavailable; that is, it cannot be utilized by the body, and is effectively inert, having no physiological action. Since it is chemically attached to the polymer, the use of any conventional physical means to break down the drug-delivery molecule (e.g., grinding, chewing, heating, extracting with organic solvents) will have no effect in releasing the drug. When the drug delivery composition reaches the stomach, an acid-mediated unmasking reaction occurs that converts a triggering functional group from its masked (e.g., protected), inactive form, into its active form. In its active form, the triggering functional group is capable of causing rupture of the covalent bond by which the drug is attached to the polymer, thereby releasing the drug to the body in its physiologically-active form. This rupture (the release reaction) may occur by way of a fragmentation reaction that is unimolecular or pseudo-unimolecular (i.e., a pseudo-first order reaction involving some species, such as acid or water that is present in large excess), or may occur by means of an intramolecular reaction involving the triggering functional group.

The rate at which the drug is released may be controlled by the rate of the unmasking reaction, by the rate of the release reaction, or by a combination of these rates. In most circumstances it will be desirable to have a rapid unmasking reaction that is followed by a slower release reaction, the rate of which can be varied in a predictable fashion. This is desirable because it allows for the drug delivery composition to be "unmasked" as soon as it reaches the stomach where pH conditions of about 1-3 prevail, and for the actual drug delivery to take place in the less acidic environment of the intestinal tract.

DETAILED DESCRIPTION

Following are definitions of terms used herein:

As used herein, "drug" refers to a biologically or pharmaceutically active substance, and includes both therapeutic and diagnostic agents. A "drug molecule moiety" is a drug attached to the remainder of the drug-delivery molecule of this invention by a covalent bond. The drug molecule moiety is based on a drug, and specifically is a drug having an available bond for covalently linking to the remainder of the drug-delivery molecule. The term "drug" may also include prodrugs known to the art.

Drugs for use in this invention are any drugs known to the art which have an amine, alcohol, or thiol moiety through which they can be bonded to the remainder of the drug-delivery molecule. Preferred drugs include drugs incorporating tertiary amines: narcotic analgesic drugs, including oxycodone, fentanyl, and propoxyphene; and mechlorethamine (an anti-neoplastic); drugs incorporating secondary amines, including methyl phenidate (Ritalin) (a central nervous system stimulant, and bis-(2-chloroethyl)amine (an anti-neoplastic); drugs incorporating alcohol group(s) including isosorbide mononitrate (a vasodilator), fluvastatin (a cholesterol lowering agent), lovastatin (a cholesterol lowering agent), codeine (a narcotic analgesic), and acetamidophenol (an analgesic); drugs incorporating a thiol group including mensa sodium (2-mercaptoethanesulfonic acid, sodium salt) (a cytoprotective agent), and captropril (an antihypertensive). All the foregoing drugs may be used in drug-delivery molecules structured to provide drug release based on nucleophilic vinylic substitution reactions, beta-elimination reactions, and fragmentation reactions. Drugs incorporating primary amines such as daunorubicin (an antineoplastic), and amlodipene (a.k.a. amlodipine, a calcium channel blocker), may also be used in drug-delivery molecules structured to provide drug release based on fragmentation and beta-elimination reactions.

The foregoing list of drugs is not intended to be exhaustive, but rather is exemplary. Some other drugs (again, not an exhaustive list) suitable for use in this invention include tertiary and secondary amine drugs such as acyclovir, cephradine, melphalan, procaine, adriamycin, and daunomycin; sympathomimetic amines such as amphetamine; benzphetamine; cathinone; desmethylsegiline; diethylpropion; ephedrine; fenfluramine; mazindol; methylenedioxyamphetamine; methylenedioxyethylamphetamine; methylenedioxymethamphetamine; mescaline; methamphetamine; methcathinone; methylaminorex; methylphenidate; pemoline; phendimetrazine; phenylepherine; phentermine; phenylpropanolamine; pseudoephedrine; selegiline; and monoamine oxidase inhibitors, phenelizine and tranylcypromine; tricyclic tertiary amine antidepressants such as Elavil; anti-Parkinson's agent, benzatropine; pirenzepine, an M1 blocker; scopolamine, a therapeutic agent for motion-sickness; cetirizine and clemastin, H1 antagonists; fluoxetine, an antidepressant, vitamin D, phenylephrine; fualfenesin; famotidine; enalapril; latanoprost; nortriptyline; desipramine; amitriptyline; imipramine; Lobeline; tacrine; atropine; physostigmine; dicycloverine; terbinifine; salmeterol; and many others.

Suitable amine, alcohol and thiol drugs for use in this invention may be found among protein drugs, desensitizing agents, vaccines, anti-infectives such as antibiotics, anti-allergenics, steroidal anti-inflammatory agents, decongestants, miotics, anticholinergics, sympathomimetics, sedatives and hypnotics, psychic energizers, tranquilizers, steroids, cardioactive agents, anti-Parkinson agents, antihypertensive agents, tricyclic antidepressants, and nutritional agents, to name only a few categories. Those skilled in the art can readily determine from the structure of any selected amine, alcohol or thiol drug, found for example in The Merck Index or the Physicians' Desk Reference, both of which are incorporated herein by reference, whether or not the drug is suitable for use in this invention.

As used herein, a "prodrug" is a molecule which is not bioactive, but which undergoes reaction(s) within a patient's body which make it bioactive. Drug-delivery molecules of this invention may be prodrugs, and such prodrugs may incorporate prodrug moieties known to the art as well as drug moieties.

The term "alkyl" includes straight-chain, branched, unsaturated, and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3 methylpentyl, 4-methylpentyl, 3,3-dimethylbutyl, 2,2-dimethylbutyl, 1,1- dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propybutyl. Alkyl groups are optionally substituted with heteroatoms or additional alkyl or aryl moieties. Lower alkyl groups are $C_1$-$C_6$ alkyl and include among others methyl, ethyl, n-propyl, and isopropyl groups.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitations: vinyl, allyl, propenyl, isopropenyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2butenyl, ethynyl, propargyl, 3-methyl-1-pentynyl, and 2-heptynyl. Unsaturated alkyl groups can optionally be substituted with heteroatoms or additional alkyl or aryl moieties.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted with heteroatoms or additional alkyl or aryl moieties.

Alkyl or aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl and triaryl groups and heterocyclic biaryl and triaryl, all of which can be optionally substituted with heteroatoms or alkyl or additional aryl groups. Preferred aryl groups have one or two aromatic rings.

"Carbocyclic aryl" refers to aryl groups in which the aromatic ring atoms are all carbons and includes without limitation phenyl, biphenyl and naphthalene groups.

"Aralkyl", refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl or triaryl" refers to heterocyclic aryls in which a phenyl group is substituted by a heterocyclic aryl group ortho, meta or para to the point of attachment of the phenyl ring to the decalin or cyclohexane. Heterocyclic biaryl and triaryl includes, among others, groups which have a phenyl group substituted with a heterocyclic aromatic ring. The aromatic rings in the heterocyclic biaryl or triaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g., unsubstituted phenyl ($—C_6H_5$), or naphthyl ($—C_{10}H_7$). Suitable substituents for aryl groups include among others, alkyl groups, unsaturated alkyl groups, halogens, OH, SH, $NH_2$, COH $CO_2H$, $OR_e$, $SR_e$, $NR_eR_f$, $CONR_eR_f$ where $R_e$ and $R_f$ independently are alkyl, unsaturated alkyl or aryl groups. Preferred substituents are OH, SH, $OR_e$, and $SR_e$ where $R_e$ is a lower alkyl, i.e., alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as —$CO_2$—, —CO—, —O—, —S—, —P—, —NH—, —CH=CH— and —$(CH_2)_n$ where n is an integer from 1 to about 5, and particularly —$CH_2$—. Examples of aryl groups having bridging substituents include phenylbenzoate. Substituents also include moieties, such as (—$CH_2)_n$—, —O—$(CH_2)_n$— or —OCO—$(CH_2)_n$, where n is an integer from about 2 to 7, as appropriate for the moiety, which bridge two ring atoms in a single aromatic ring as, for example, in a 1,2,3,4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethyl propoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3- methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethylpropoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Et" refers to "ethyl." "Ph" refers to "phenyl."

A "masking group" as used herein is a moiety that is attached to a reactive atom or group which prevents the reactive atom or group from reacting with other atoms on the same or other molecules. Preferred reactive atoms and groups herein are O, S and NR where R is H, aryl or alkyl. Those skilled in the art will recognize that masking groups are a subset of what are commonly termed "protecting groups," and that masking groups may be described as protecting groups for O, S, and NR that may be removed under particular physiological conditions found in the body of living organisms. Masking group for these reactive atoms are known to those skilled in the art, as are conditions including pH under which they may be removed, as described, for example, in Greene, T. W. and Wuts, P. G. M., "Protective Groups in Organic synthesis, 3rd Ed. (John Wiley & Sons, New York, 1999), Chapter 3, "Protection for the Hydroxyl Group, pp. 17-292, Chapter 6, "Protection for the Thiol Group," pp. 454-493, and Chapter 7, "Protection for the Amino Group," pp. 494-653, all of which are incorporated herein by reference. Preferred masking groups of this invention are —C(O)R, —C(O)OR, —C(O)NRR, —C(S)R, —C(S)OR, —C(O)SR, —C(S)NRR, —CRR(OR), —CR=CRR, —C(OR)—CRR, and —CR(OR)(OR). Some masking groups may also be enzymatically cleaved from the molecules by enzymes in the organism.

Masking groups which are "easily removed" or "easily detachable" from the reactive atom or group are those that are readily hydrolyzed under acidic or basic conditions. Examples of easily-removed masking groups are acetals, ketals, orthoesters, enol ethers, enol thioethers, and many enamines for removal under acidic conditions, and many esters for removal under mildly basic conditions. Masking groups which are "less easily removed" are those which hydrolyzed with greater difficulty under acidic or mildly basic conditions. Examples of less-easily removed masking groups are many esters, thioesters, carbamates, ureas, and phosphate esters.

A "triggering group" or "reaction-enhancing moiety" as used herein is a moiety consisting of or comprising a reactive atom which is capable of reacting with other atoms of the same or other molecules in at least one selected environment. Preferred triggering atoms and groups are O, S, or NR where R is H, alkyl or aryl.

A triggering group "near" a nitrogen atom of an amine drug moiety, or an oxygen atom of an alcohol drug moiety, or a sulfur atom of a thiol drug moiety, is sufficiently close to said nitrogen, oxygen, or sulfur atom, to undergo intermolecular reaction with the atom to which the drug moiety is attached under selected conditions. Generally this means that the number of atoms between the triggering atom and the carbon to which the drug is attached is three to eight, leading to intramolecular reactions having ring sizes of up to ten members.

As used herein a spacer is a series of atoms in a chain separating the triggering atom and the carbon to which the drug is attached. Preferably the spacer is Qn as defined herein, namely, Q is a series of atoms of chain length n where n is 1 to about 6 or 7, which can be aryl, aralkyl, —O—, —S—, NR where R is H, alkyl, C(O), and unsaturated alkyl or aryl. Preferably no O—O, S—S or S—NR bonds are incorporated into the spacer. Portions of Qn may be connected to other portions of Qn or to other parts of the controlled release device, that is, the spacer may incorporate one or more rings, whether they be saturated, unsaturated or aromatic.

As used herein, a "carbanion stabilizer" is an electron-withdrawing group which stabilizes a nearby negative charge. Preferred carbanion stabilizers of this invention are compatible moieties selected from the group consisting of —C(O)R, —C(O)OR, —C(O)NRR, —CN, —NO$_2$, —P(O)(OR)(OR), —P(O)(NRR), —S(O)R, —S(O)$_2$R and aryl, where each R is, independently, H, alkyl or aryl, and where two R groups can be connected to another R group or to another atom of the drug-delivery molecule through alkyl, aryl, —O—, —S— or —NR— where R is H, alkyl or aryl, or —C(O)—. "Carbanion stabilizers" may also be incorporated as part of a chain, where they are preferably selected from the group —C(O)—, —C(O)NR—, —C(S)—, —C(O)O—, —S(O)—, —S(O)$_2$—, —P(O)(OR)—, —P(O)(NRR)—, —P(O)(OR)NR—.

An "electron-withdrawing atom or group" is a substituent that draws electrons to itself more than a hydrogen atom would if it occupied the same position. Exemplary electron-withdrawing groups include halogen, nitro, cyano, hydroxyl, fluoroalkyl, perfluoroalkyl, nitrile, carboxyl, carboxylic ester, amide, sulfoxide, sulfone, carbonyl and ammonium groups. The carbonyl groups may exist as ketones or as aldehydes. "Halogen" according to the invention means fluorine, chlorine, bromine, or iodine.

A "nucleophile" or "nucleophilic group" comprises an atom or an atom part of a group of atoms that has an unshared pair of electrons that are capable of taking part in nucleophilic substitution reactions, thereby replacing another atom. Nucleophiles may be involved in substitution reactions at saturated carbons and unsaturated carbons. Thus, one familiar with the art recognizes that these reactions include the well known $S_N$ reactions, as well as nucleophilic vinylic substitution, nucleophilic aromatic substitution, reactions at the electrophilic carbon of esters, thioesters, amides, thioamides, carbamates, thiocarbamates, ureas and thioureas. These reactions also include the substitution reaction by nucleophiles at phosphorous species, such as phoshphate esters, thiophosphate esters, phosphoramidates, phosphonates, thiophosphonates and thiophosphoramidates. Those skilled in the art also know that the nucleophilicity of an atom is dependent on many factors, including basicity, polarizability, direct attachment to another atom having a lone pair of electrons (the alpha effect), steric factors, the solvent in which the substitution reaction takes place, the pH of the medium, the presence of hydrogen bond donors, whether intermolecular or intramolecular, and Lewis acids capable of complexing the nucleophilic atom.

An "electron-donating atom or group" is a substituent that draws electrons to itself less than a hydrogen atom would if it occupied the same position. Example electron-donating groups include alkoxy groups, for example, methoxy and ethoxy groups. In general —N— or groups containing —N— are more electron donating than neutral —OR— or —SR groups, though —O— is often more electron donating than —N— groups. It is also well known that substituents on an electron-donating atom may greatly influence the donor ability through their own electron donating or electron-withdrawing characteristics.

Structures are provided herein with variable components describing a plurality of molecules. These structures define classes of compounds of this invention. Each value for each variable defines a further class of compounds of this invention, and each specific embodiment defined by a specific value for each variable defines a further class of compounds of this invention. This invention includes any class or combination of classes of compounds defined herein.

An "amino drug" or "amine drug" as used herein is a drug comprising at least one amine group, which may be a tertiary, secondary, or primary amine group, the nitrogen atom of which may be attached to drug-delivery moieties of this invention. It may also include the nitrogen of heterocyclic amines, such as pyridine or imidazole.

An "alcohol drug" as used herein is a drug comprising at least one alcohol group, the oxygen atom of which may be attached to drug-delivery moieties of this invention.

A "thiol drug" as used herein is a drug comprising at least one thiol group, the sulfur atom of which may be attached to drug-delivery moieties of this invention.

A given drug may be classed as more than one of an amine, alcohol, or thiol drug.

The terms "group" and "moiety" are used interchangeably herein.

"Polymer" or "polymeric moiety" as used herein include biodegradable and non-biodegradable polymers, preferably the latter. A polymeric moiety is a polymer having an available bond for covalent attachment to another chemical group. A polymeric moiety is "based on" a polymer when it consists of the polymer attached by such an available covalent bond to the remainder of the drug-delivery molecule.

It is preferable that the polymeric moiety for use in a drug-delivery molecule of this invention be based on a polymer which is nonabsorbable or essentially nonabsorbable in the patient's body. Such polymeric materials are not absorbed or metabolized by the body and thereby are beneficial for use as a drug "carrier" as such polymers are substantially physiologically inactive. For example, polymers which are of high molecular weight, e.g., about 1,000-160,000 Mw, charged or crosslinked polymers or polymers which are insoluble under physiologically acidic conditions (such as by crosslinking), eliminate or significantly reduce transportation of the polymer across the gut wall. Exemplary polymeric materials include polyamines, polybutadienes, polystyrenes, polyethylene, polymethacrylate, polyester, and polyamide, copolymers of the foregoing, 1,3-dienes, polysaccharides, hydroxypropyl-methylcellulose, maleic copolymers, and any polymer having derivatizable olefinic bonds, and including polymers having alkyl, aryl, or other substituents, and copolymers of any of the foregoing. The term "copolymer" is used herein to mean mixed polymers (such as polybutadiene) which contain more than one polymer.

Another group of preferred polymeric materials includes polymers which are adapted to swell at pH values of about 1 to 7. Exemplary polymeric materials which manifest such swelling characteristics include polyamines and their quaternary salts.

In order to render certain of such polymers insoluble under acidic conditions, the polymers can be crosslinked by methods well known in the art. For example, crosslinking agents can be employed or free radical crosslinking of the polymer can be performed. The crosslinking is performed to an extent sufficient to render the polymer insoluble without significantly affecting the release characteristics of the polymer. Crosslinking is not necessary to make the polymer insoluble as solubility of the polymer can also be affected by the molecular weight of the polymer.

The crosslinking agent can be any suitable crosslinking agent which can crosslink the polymer selected for use in this invention. The selection of a crosslinking agent is within the level of skill in the polymer art. Depending upon the polymer selected the crosslinking agent can be a dialdehyde, diacid, disilane, dihaloxylene, tri(halomethyl)benzene, dihaloalkane, dihaloalkene, diallylhalide, or any polyaromatic, aliphatic or allylic halide, and the like.

Certain of the polymers that can be used herein can also be modified by attaching auxiliary groups which can impart certain properties such as gastric retention, hydrophilicity, crystallinity and the like. For example, auxiliary groups such as dialkylamino groups or quaternized ammonium salts can be employed to control certain properties, such as hydrophilicity, swelling, crystallinity and the like to effect the drug release rate.

The remainder of the drug-delivery molecule is attached to the polymer by covalently bonding to the polymeric material, such as to the polymer backbone or to certain pendant functional groups, by way of a covalent bond which is stable under physiological conditions.

"Polymeric monomers" as used herein include any monomer which can undergo polymerization, preferably monomers making up the polymers described above.

A statement that a molecule is "stable" under certain conditions means that the molecule does not break apart under such conditions.

A wavy line is sometimes used in structures depicted herein to indicate a bond attaching a cis or trans substituent. A solid bond, however, does not preclude any possible conformation, including cis or trans.

The term "compatible moiety" refers to a moiety which can exist in a particular designated place in a defined structure, with which structure it is said to be "compatible," e.g., the moiety has the proper number of available bonds, or is not too bulky to exist in its designated place.

As used herein, the term "patient" refers to a human or animal, preferably a mammal.

The drug moiety is present in the compositions of this invention in an amount that is sufficient to prevent, cure and/or treat a condition for a desired period of time for which the composition of this invention is to be administered, and such an amount is referred to herein as "an effective amount." As is well known, particularly in the medicinal arts, effective amounts of medicinal agents vary with the particular agent employed, the condition being treated and the rate at which the composition containing the medicinal agent is eliminated from the body, as well as varying with the subject in which it is used, and the body weight of that subject. An effective amount is that amount which in a composition of this invention provides a sufficient amount of the active ingredient to provide the requisite activity of the active ingredient in the body of the treated subject for the desired period of time.

Inasmuch as amounts of particular active ingredients that are suitable for treating particular conditions are generally known, it is a relatively easy laboratory task to formulate a series of release compositions of this invention containing a range of such active ingredients to determine the effective amount of such an active ingredient for a particular composition of this invention. Based upon a reading of the description herein, it is within the skill of the art to select an amount of any particular active ingredient and to covalently bond such an amount to the remainder of a drug-delivery molecule of this invention for delivering an effective amount of such active ingredient. While the effective amount for all active ingredients cannot be stated, typical compositions of this invention can contain about one microgram to about one gram of active ingredient per dose administered. More preferably, a composition of this invention can contain about one microgram to about 250 milligrams per dose.

The drugs can be covalently bonded to the remainder of the drug-delivery molecules of this invention according to the teachings of the present invention for release in an acidic or basic environment depending on the desired physiological action of the drug, systemic side effects associated with each drug, decomposition rate of the drug in a particular environment and other factors well known in the medicinal arts.

In general, the preferred method for administration of drugs is via an enteric, and particularly oral, route. This provides ease of administration and an associated high level of patient compliance. However, many drugs currently cannot be effectively delivered via an oral route. Examples of such agents include peptide and protein pharmaceuticals include calcitonin, erythropoietin, thrombopoietin, granulocyte colony stimulating factor, stem cell factor, LHRH analogs, somatostatin, insulin, interferons, plasminogen activator inhibitors, recombinant antibodies and monoclonal antibodies. For example, delivery of species of DNA and RNA (sense or antisense), antibodies, vaccines as well as more traditional chemotherapeutic agents is contemplated. Thus, the term "drug" is to be understood as encompassing simple organic or inorganic compounds, nutritional agents and imaging agents such as metals, radioactive isotopes, radio-opaque or radiolucent agents. Examples of "traditional" chemotherapeutic agents include hormones, polysaccharides, such as heparin, antibiotics, anti-inflammatory compounds, antivirals, vasoactive and neuroactive agents, anticoagulants, immunomodulating agents, cytotoxic agents, steroids, decongestants, anaesthetics, sedatives and any other agents required to be delivered to a patient for therapeutic, prophylactic or diagnostic purposes. This list of classes of drugs is not intended to be exhaustive.

In addition, the drugs according to the invention can occur in various forms, for example as charged or uncharged molecules, as components of molecular complexes, as salts, amines, ethers, esters, or amides, or as other derivatives or prodrugs of the drugs concerned.

The present invention is not limited to enteric delivery of pharmaceutical agents. For example, parenteral delivery of pharmaceutical agents can also benefit from the present invention, such as when a pharmaceutical agent must penetrate barriers (other than the gastrointestinal mucosa) within the body in order to reach the target organ or target site. The blood-brain barrier is one example of such a barrier. In addition, a pharmaceutical agent may be delivered to, and retained at, a particular active site.

A drug is said to be "encapsulated" or "embedded" within a polymer when it is not covalently bound to the polymer but is surrounded by material making up the polymer so that it cannot escape therefrom under physiological conditions unless the permeability of the polymer is enhanced.

This invention provides methods for controlled delivery of an amine, alcohol, or thiol drug to a patient comprising providing a drug-delivery molecule comprising an amine, alcohol, or thiol drug molecule moiety attached by way of the drug amine nitrogen, alcohol oxygen, or thiol sulfur to a carbon atom of the remainder of the drug-delivery molecule by a covalent bond which is stable under physiological conditions. The drug-delivery molecule also comprises a masked release-enhancing moiety. The drug-delivery molecule is exposed to selected conditions under which an unmasking reaction occurs; whereupon the release-enhancing moiety facilitates breaking of the covalent bond attaching the drug molecule moiety to the remainder of the drug-delivery molecule, and the drug is released.

The release-enhancing moiety may be a nucleophilic moiety, an electron-donating moiety or an electron-withdrawing moiety, as more fully described below.

The selected conditions may be any conditions inside a patient's body, such as acidic conditions within a patient's stomach or more basic conditions within a patient's intestine.

The covalent bond between the drug moiety and the remainder of the drug-delivery molecule is preferably broken by an intramolecular reaction, such as between the release enhancing moiety and the carbon atom to which the drug molecule moiety is covalently attached.

To prevent the drug from being active before the desired time and place of release inside a patient's body, another moiety, preferably a polymeric moiety, is covalently attached to the drug-delivery molecule.

The rate of release of the drug from the drug-delivery molecule can be controlled by a number of means including controlling the unmasking reaction, or controlling the breaking of the covalent-bond attaching the drug molecule moiety to the remainder of the drug-delivery molecule. The methods for controlling the rate of release of the drugs discussed below can be utilized singly or in any required combination.

The unmasking reaction can be controlled by selecting a more easily hydrolyzable masking group for the drug-delivery molecule when a faster rate is desired and a less easily hydrolyzable masking group when a slower reaction is desired.

The release reaction can be used to control the release rate of the drug by providing a more powerful release-enhancing moiety when a faster rate is desired, and a less powerful release-enhancing moiety when a slower rate is desired. When the release-enhancing moiety is an electron donor or an electron-withdrawing moiety, a more or less powerful electron donor or electron-withdrawing moiety can be used to control the'release rate. When the release rate depends on a nucleophilic release-enhancing moiety, a more nucleophilic moiety can be used for a faster rate, and a less nucleophilic moiety can be used for a slower rate.

With one class of drug-delivery molecules of this invention involving intramolecular vinylic substitution reactions to release the drug, the drug-delivery molecule comprises a single bond between the drug molecule moiety and a $C=C$ moiety of the remainder of the drug-delivery molecule, and the method comprises controlling the release rate of the drug by controlling the rate of breaking the covalent bond by which the drug molecule moiety is attached by selecting a spacer chain or spacer moiety between the carbon of the $C=C$ moiety that the drug molecule moiety is attached to and the release-enhancing moiety which is three atoms long when a faster rate is desired, and longer or shorter than three atoms long when a slower rate is desired.

The release rate can be fine-tuned by selecting a spacer chain or spacer moiety between the $C=C$ moiety and the release-enhancing moiety which has more alkyl and/or aryl substituents when a faster rate is desired, and fewer such substituents when a slower rate is desired.

With another class of drug-delivery molecules of this invention involving drug release by fragmentation reactions, the release-enhancing moiety is an electron-donating moiety and the amine nitrogen, alcohol oxygen, or thiol sulfur of the drug molecule is connected by a single covalent bond to a carbon which is connected by a single covalent bond to an aryl group comprising a phenyl ring having a masked release-enhancing moiety in an ortho or para relationship to the drug molecule moiety.

In addition to controlling the release rate of the drug by selecting a suitable masking group as described above, the release rate of the drug can be controlled by controlling the rate of breaking of the covalent bond between the drug molecule moiety and the remainder of the drug-delivery molecule (the release reaction) by providing a more powerful electron-donating moiety when a faster rate is desired and a less powerful electron-donating moiety when a slower rate is desired.

The rate of the release reaction can also be controlled by providing the drug-delivery molecule with one or more sterically bulky groups on the phenyl ring ortho to the carbon to which the drug molecule moiety is attached or on the carbon to which the drug molecule moiety is attached when a faster rate is desired and providing less sterically bulky groups or no sterically bulky group when a slower rate is desired.

In a two-stage unmasking method, similar drug-delivery molecules having masked release-enhancing moieties ortho or para on a phenyl ring to the carbon to which the drug molecule moiety is attached are used. The drug-delivery molecule comprises a first release-enhancing moiety masked by a first masking group, and a second release-enhancing moiety masked by a second masking group, and the method comprises exposing the drug-delivery molecule to selected conditions wherein the second masking group is removed to expose the second release-enhancing moiety, allowing the second release-enhancing moiety to react in an intramolecular reaction wherein the second release-enhancing moiety replaces the first release-enhancing moiety on the first masking group, so that the second release-enhancing moiety and first masking group form a ring that is not directly attached to the first release-enhancing moiety, thereby exposing an unmasked first release-enhancing moiety, whereby release of the drug is facilitated.

In this two-stage unmasking method, the release rate of the drug can be controlled by providing first and/or second masking groups which are easily hydrolyzed when a faster rate is desired and less easily hydrolyzed when a slower rate is desired. The unmasking reactions can be separately controlled to occur under different conditions, if desired.

The release reaction can also be used to control the rate of release of the drug by providing, in the drug-delivery molecule, a spacer chain or spacer moiety between the second release-enhancing moiety and the first masking group which is three atoms long when a faster rate is desired, and longer or shorter than three atoms long when a slower rate is desired. The release reaction rate can be fine tuned by selecting a spacer chain or spacer moiety which has more alkyl and/or aryl substituents when a faster rate is desired, and fewer such substituents when a slower rate is desired.

The rate of the release reaction can also be controlled by providing a more powerful electron-donating first release-enhancing moiety when a faster rate is desired and a less powerful electron-donating first release-enhancing moiety when a slower rate is desired, and/or by providing a more nucleophilic second release-enhancing moiety when a faster rate is desired and a less nucleophilic second release-enhancing moiety when a slower rate is desired.

With a further class of drug-delivery molecules of this invention drug release involves a beta-elimination reaction, and the drug-delivery molecule comprises a drug molecule moiety attached by a single covalent bond by way of its amine nitrogen, alcohol oxygen or thiol sulfur to a first carbon atom which is in turn attached by a single covalent bond to a second carbon atom having at least one hydrogen substituent and at least one masked or unmasked electron-withdrawing moiety, and the method comprises exposing the drug-delivery molecule to conditions under which the electron-withdrawing moiety acts to facilitate removal of the hydrogen substituent as H+, which in turn facilitates breaking of the covalent bond attaching the drug molecule moiety to the drug-delivery molecule, thereby releasing the drug.

Preferably, the electron-withdrawing group is masked and the method comprises exposing the drug-delivery molecule to conditions under which the electron-withdrawing group is unmasked. The rate of drug delivery can be controlled by controlling the rate of the unmasking reaction, by using a masking group which is easily hydrolyzed to expose the electron-withdrawing moiety when a faster rate is desired, and which is less easily hydrolyzed when a slower rate is desired.

The rate of drug delivery can also be controlled by providing two masked electron-withdrawing groups attached to the second carbon atom when a faster rate is desired. As with other classes of drug-release molecules of this invention, the rate of the unmasking reaction can be controlled by masking one or both electron-withdrawing groups with masking groups which are easily hydrolyzed to expose the electron-withdrawing group they mask when a faster rate is desired, and which are less easily hydrolyzed when a slower rate is desired.

The rate of drug release can also be controlled by controlling the rate of the release reaction, using a more powerful electron-withdrawing moiety when a faster rate is desired and a less powerful electron-withdrawing moiety when a slower rate is desired.

In further embodiments of this invention, a drug is encapsulated or embedded in a polymer, rather than being covalently bonded to a polymer. The polymer comprises subunits comprising a substituent containing a masked release-enhancing moiety positioned such that an intramolecular reaction can occur between the release-enhancing moiety and a carbonyl or phosphoryl group within the subunit. The polymer is exposed to selected conditions under which the release-enhancing moiety is unmasked, which allows the release-enhancing moiety to react in an intramolecular reaction with the carbonyl or phosphoryl group, whereby the polymer chain is broken, facilitating escape of said drug. Up to about 1,000, about 10,000 or about 250,000 of these subunits may be present in such a drug-delivery polymer. The subunits may be interspersed with monomers of other polymers, preferably non-biodegradable polymers, or biodegradable polymers which degrade more slowly under the selected conditions than the subunits which undergo intramolecular breakdown reactions. The subunits of this invention can also be used to crosslink polymer chains made up of other polymeric monomers, again preferably non-biodegradable polymer chains or polymer chains which degrade more slowly than the subunits of this invention.

Useful release-enhancing moieties for the polymer subunits of this invention are selected from the group consisting of —O—, —S— or —NR—, wherein R is H, aryl or alkyl. Again, the rate of drug release can be controlled by masking the release-enhancing moiety with a masking group which is easily hydrolyzed to expose the release-enhancing moiety when a faster rate is desired, and which is less easily hydrolyzed when a slower rate is desired. The intramolecular reaction causing breaking of the polymer chain can also be used to control the rate of drug release, and this reaction can be controlled by providing a spacer chain or spacer moiety between the release-enhancing moiety and the carbonyl or phosphoryl which is three atoms long when a faster rate is desired and longer or shorter than three atoms long when a slower rate is desired. The reaction can be further fine tuned by selecting a spacer chain or spacer moiety which has more alkyl and/or aryl substituents when a faster rate is desired, and fewer such substituents when a slower rate is desired. The intramolecular reaction can also be controlled by using a more powerful nucleophilic release-enhancing moiety when a faster rate is desired and a less powerful nucleophilic release-enhancing moiety when a slower rate is desired.

Controlled Release Molecules Based on Nucleophilic Vinylic Substitution Reactions.

In one embodiment of this invention, an amine, alcohol or thiol drug is incorporated into the controlled-release molecule. In an embodiment where the drug is a tertiary amine drug, it is incorporated into the drug-delivery molecule as a vinyl quaternary ammonium salt. The carbon of the vinyl group to which the drug is not bound is directly attached to a carbanion-stabilizing group that is capable of stabilizing an adjacent negative charge. On either of the two carbons of the vinyl group there is a spacer group that is terminated by a nucleophilic atom, which in turn is attached to a masking group. Exposure to a selected set of physiological conditions (determined by the identity of the masking group) leads to cleavage of the masking group, exposing the unmasked nucleophilic atom; this attacks the vinylic carbon bearing the drug, leading to replacement of the drug by the nucleophilic atom, thereby releasing an unattached, bioavailable drug molecule.

One class of drug-delivery molecules of this invention, useful for drug release by vinylic substitution reaction, are molecules selected from the group consisting of compounds of the formula:

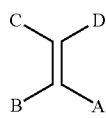

wherein A is a moiety selected from the group consisting of tertiary amine drug ion moieties, secondary amine drug moieties, primary amine drug moieties, alcohol drug moieties and thiol drug moieties connected to the vinyl carbon through the amine nitrogen, alcohol oxygen or thiol sulfur;

wherein one of B, C or D is a masked triggering moiety consisting essentially of a triggering atom or group selected from —O—, —S—, or —NR— wherein R is H, alkyl or aryl, linked to a masking group, and wherein said masked triggering moiety is optionally linked to the vinyl carbon through a spacer and/or a carbanion stabilizer;

wherein at least one of C or D must comprise a carbanion stabilizer; and wherein B and C and/or C and D taken together may be aryl or cycloalkyl;

wherein another of B, C or D is a carbanion stabilizer, or is a polymeric moiety optionally connected to the vinylic carbon through a linking moiety and/or a carbanion stabilizer; and wherein the last of B, C or D is a carbanion stabilizer or a reactivity-modifying group; and stereoisomers, pharmaceutical salts, and mixtures of the foregoing.

More specifically, this invention provides a drug-delivery molecule of claim 1 wherein:

one of B, C or D is -Qn-J-M or —Z'-Qn-J-M, wherein each Q is, independently, a moiety selected from alkyl and aryl moieties, —O—, —S—, —NR—, and —C(O)— provided however that Q does not include O—O, S—S or S—NR bonds;

wherein R is H, alkyl or aryl, and two R groups may be connected to another R group or to another atom of the drug-delivery molecule through alkyl, aryl, —O—, —S—, —NR—, or —(O)—, provided there are no O—O, S—S, or S—NR bonds;

wherein n is 1-6;

wherein J is —O—, —S—, or —NR—;

wherein R is as defined above;

wherein M is a masking group selected from the group consisting of —C(O)R, —C(O)OR, —C(O)NRR, —C(S)R, —C(S)OR, —C(O)SR, —C(S)NRR, —CRR(OR), —CR═CRR, —C(OR)═CRR, and —CR(OR)(OR);

wherein each R is, independently, as defined above;

wherein Z' is a carbanion stabilizer selected from the group consisting of —C(O)—, —(O), —S(O)₂— —P(O)(OR)— —P(O)R—, —P(O)(NRR)—, and aryl;

wherein each R is, independently, as defined above;

wherein another of B, C or D is Z— or [P]-Um-Z'— or [P]-Um-;

wherein Z' is as defined above;

wherein Z is a carbanion stabilizer selected from the group consisting of aryl, —C(O)R, —C(O)OR, —C(O)NRR, —CN, —NO₂, —P(O)(OR)(OR), —P(O)(NRR), —S(O)R, and —S(O)₂R;

wherein each R is, independently, as defined above;

wherein [P] is a pharmaceutically acceptable polymeric moiety, optionally comprising repeats of the moiety depicted for the remainder of the drug-delivery molecule, said repeats comprising the drug moiety and said repeats being spaced along said polymeric moiety;

wherein each U is, independently, selected from the group consisting of alkyl and aryl moieties, —O—, —S—, and —NR—, and —C(O)—, provided, however that U does not include O—O, S—S or S—NR bonds;

wherein R is as defined above; and wherein m is 0-50; and wherein one of C or D must comprise Z or Z' directly attached to the vinylic carbon; and wherein the last of B, C or D is —Z or is selected from the group consisting of H, alkyl and aryl moieties, —CN, —C(O)R, —C(O)OR, —C(O)NRR, —S(O)R, —S(O)₂R, —P(O)(OR)(OR), and —P(O)(OR)(NRR);

wherein each R is, independently, as defined above; and stereoisomers, pharmaceutical salts, and mixtures of the foregoing.

In one class of the above drug-release molecules, A is selected from the group consisting of

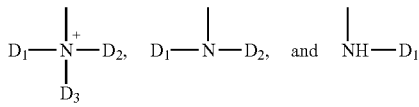

wherein $D_1$, $D_2$ and $D_3$ are substituents of amine drug molecules, and

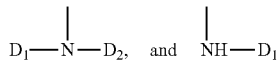

may be present as the corresponding ammonium salts.

Polymer moieties used in this invention are preferably non-biodegradable polymeric moieties having a molecular weight between about 500 and about 1,000,000, more preferably about 100,000 to about 600,000. Suitable non-biodegradable polymers are known to those skilled in the art, and include without limitation, polystyrene, polyamine, polybutadiene, polymethacrylate, polyethylene, polyacrylate, polyamide, 1,3-dienes, methylcellulose, polyamino acids and polysaccharides, and alkyl and aryl-substituted derivatives thereof, and copolymers of any of the foregoing.

The polymeric moiety may also be from a biodegradable polymer, and again preferably has a molecular weight between about 500 and about 1,000,000, preferably between about 100,000 and about 600,000. Suitable biodegradable polymers are known to the art and include without limitation polyglycolate, polylactate, polyamino acids and polysaccharides.

The drug-delivery molecules of this invention may include a polymeric moiety, or the polymeric moiety may be absent, to give a prodrug in which the drug will no be active until released. Preferably, the remainder of the prodrug is chosen such that after release of the drug, the remainder of the prodrug molecule is non-toxic.

Suitable drugs for use in this invention include protein drugs, desensitizing agents, vaccines, anti-infectives such as antibiotics, anti-allergenics, steroidal anti-inflammatory agents, decongestants, miotics, anticholinergics, sympathomimetics, sedatives and hypnotics, psychic energizers, tranquilizers, steroids, cardioactive agents, anti-Parkinson agents, antihypertensive agents, and nutritional agents, to name only a few categories. Narcotic analgesic drugs which are amine, alcohol, or thiol drugs, and tertiary amine tricyclic antidepressants are preferred classes of drugs useful in this invention.

Specific drugs useful in this invention include narcotic analgesic drugs such as oxycodone, fentanyl, and propoxyphene; mechlorethamine (an anti-neoplastic); drugs incorporating secondary amines, including methyl phenidate (Ritalin) (a central nervous system stimulant, and bis-(2-chloroethyl)amine (an anti-neoplastic); drugs incorporating alcohol group(s) including isosorbide mononitrate (a vasodilator), fluvastatin (a cholesterol lowering agent), lovastatin (a cholesterol lowering agent), codeine (a narcotic analgesic), and acetamidophenol (an analgesic); drugs incorporating a thiol group including mensa sodium (2-mercaptoethanesulfonic acid, sodium salt) (a cytoprotective agent), and captropril (an antihypertensive); drugs incorporation primary amines such as daunorubicin (an antineoplastic), and amlodipene (a.k.a. amiodipine, a calcium channel blocker), sympathomimetic amines such as amphetamine; benzphetamine; cathinone; desmethylsegiline; diethylpropion; ephedrine; fenfluramine; mazindol; methylenedioxyamphetamine; methylenedioxyethylamphetamine; methylenedioxymethamphetamine, mescaline, methamphetamine, methcathinone, methylaminorex; methylphenidate; pemoline; phendimetrazine; phenylepherine; phentermine; phenylpropanolamine; pseudoephedrine; selegiline; and monoamine oxidase inhibitors, phenelizine and tranylcypromine; tricyclic tertiary amine antidepressants such as Elavil; anti-Parkinson's agent, benzatropine; pirenzepine, an M1 blocker; scopolamine, a therapeutic agent for motion-sickness; cetirizine and clemastin, H1 antagonists; fluoxetine, an antidepressant, vitamin D; phenylephrine; fualfenesin; famotidine; enalapril; arnlodipene; latanoprost; nortriptyline; desipramine; amitriptyline; imipramine; Lobeline; tacrine; atropine; physostigmine; dicycloverine; terbinifine; salmeterol; and many others.

A further class of drug-delivery molecules of this invention are selected from the group of molecules having the formulas:

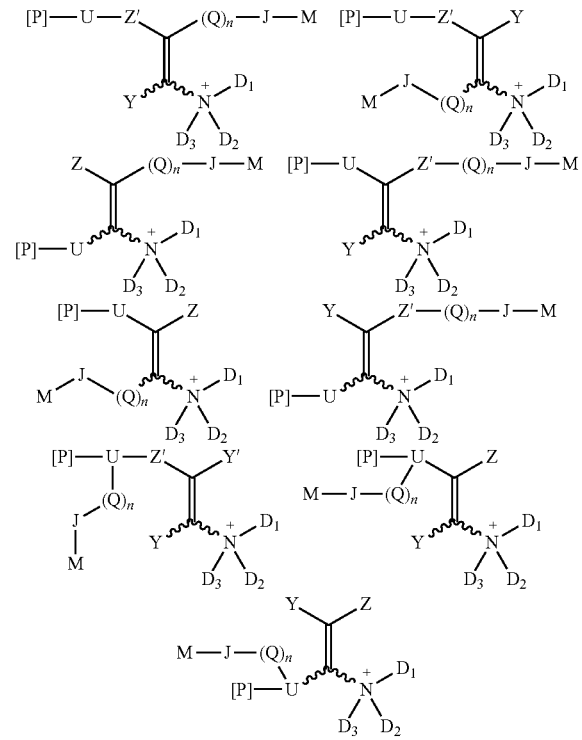

wherein Y and Y' are, independently, reactivity-modifying groups selected from the group consisting of H, alkyl, aryl, —CN, —C(O)R, —C(O)OR, —C(O)NRR, —S(O)R, —S(O)$_2$R, —P(O)(OR)(OR), and —P(O)(OR)(NRR); and any of the foregoing groups attached to —U—[P];

wherein each R is, independently, H, alkyl or aryl, and two R groups may be connected to another R group or to another atom of the drug-delivery molecule through alkyl, aryl, —O—, —S—, or —NR— where R is H, alkyl or aryl, or —C(O)—, provided there are no O—O, S—S, or S—NR bonds;

wherein the remaining substituents are as defined above, and $D_1$, $D_2$ and $D_3$ are substituents of a tertiary amine drug.

Drug-delivery molecule of this invention also include molecules selected from the group consisting of molecules comprising secondary amine drug moieties having the formulas:

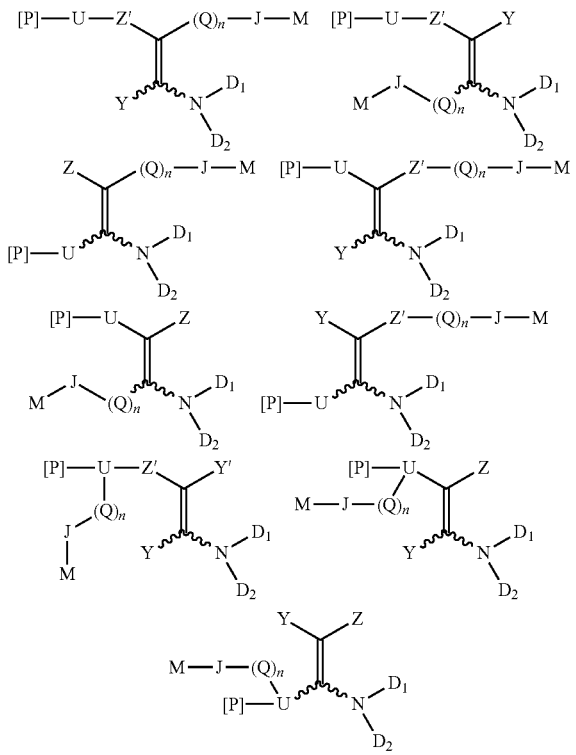

wherein the substituents are as defined above and $D_1$ and $D_2$ are substituents of a secondary amine drug.

Drug-delivery molecules of this invention include molecules selected from the group consisting of molecules comprising drug molecule moieties of primary amine, alcohol or thiol drugs, having the formulas:

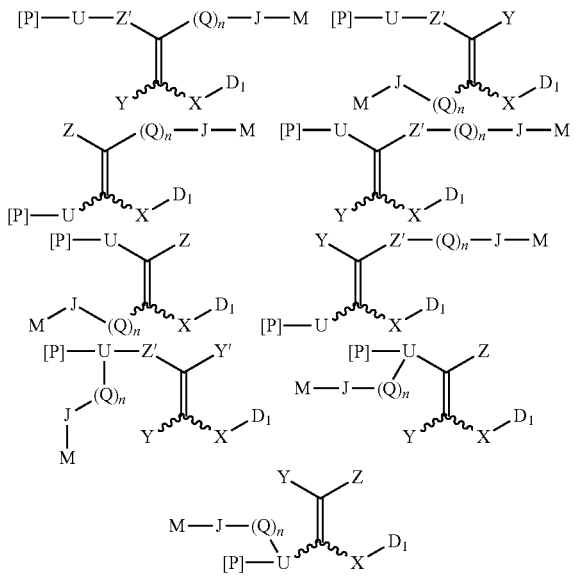

wherein the substituents are as defined above, and X is —NH—, —S— or —O— and $D_1$ is a substituent of a primary amine, alcohol or thiol drug.

Two specific nucleophilic vinylic substitution drug-delivery molecules for fentanyl have at least some repeating units having the following structures:

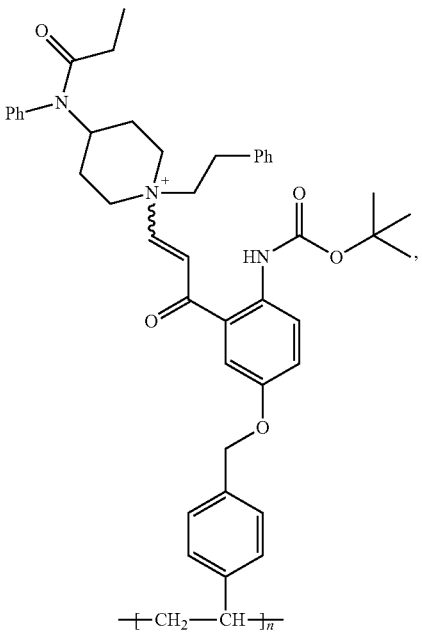

n is about 10 to about 10,000; and

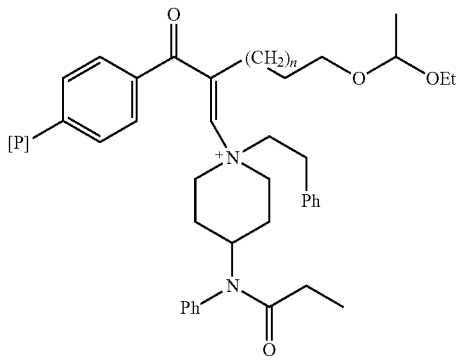

wherein [P] is as defined above; and wherein n is 0-2.

The operation of a controlled-release molecule released by vinylic substitution is illustrated in Scheme 1 for the drug oxycodone. In this case, the polymer is a polystyrene derivative, the masking group is an acetal, and the nucleophilic atom it masks is an oxygen. The possibility of a variable number of spacer atoms (O) is indicated by -( )$_n$- which stands for —(CH$_2$)—.

Scheme 1 Operation of the Oxycodone Drug Delivery Device

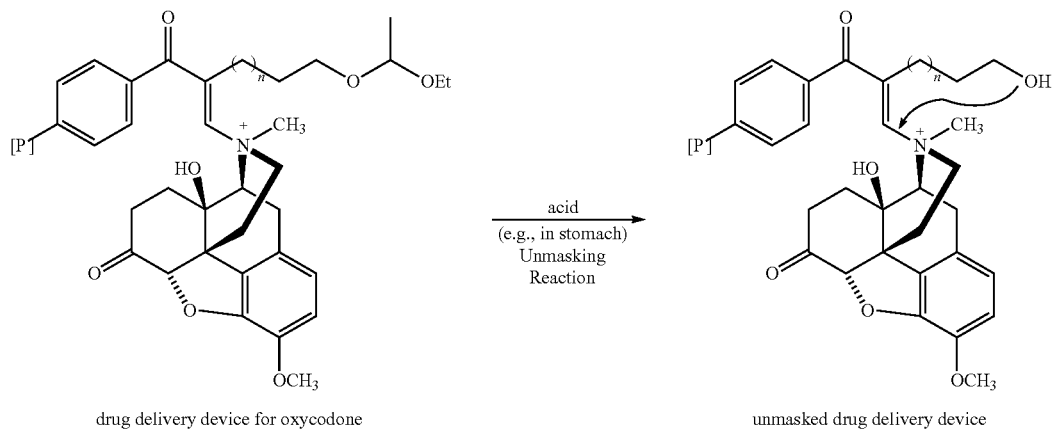

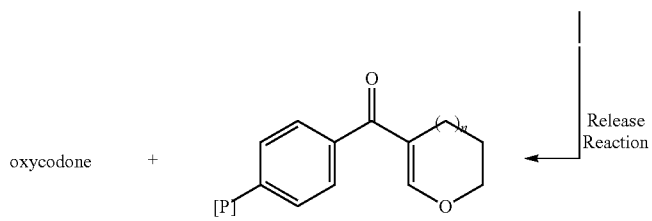

Another class of drug-delivery molecules of this invention are molecules useful for drug release by means of fragmentation reactions, selected from the group of molecules having the formulas:

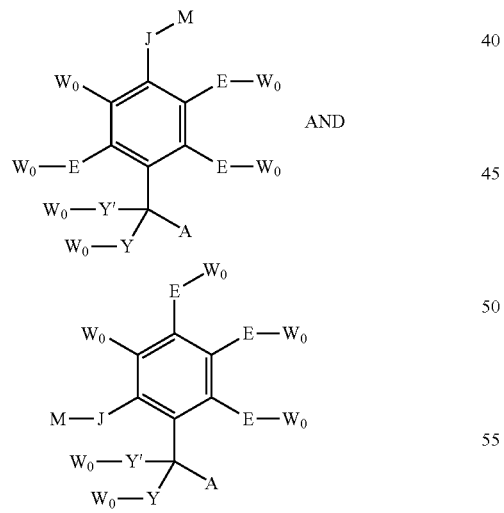

AND wherein A is a moiety selected from the group consisting of tertiary amine drug ion moieties, secondary amine drug moieties, primary amine drug moieties, alcohol drug moieties, and thiol drug moieties attached through the amine nitrogen, alcohol oxygen, or thiol sulfur;

wherein W is —Um—[P]— wherein [P] is a pharmaceutically acceptable polymeric moiety, optionally comprising repeats of the moiety as depicted for the remainder of the drug-delivery molecule, said repeats comprising the drug moiety, and said repeats being spaced along said polymeric moiety;

wherein each U is, independently, selected from the group consisting of alkyl and aryl moieties, —O—, —S—, —NR—, where R is H, aryl, or alkyl and —C—(O)— provided, however, that U does not include O—O, S—S or S—NR bonds;

wherein R is H, alkyl or aryl, and two R groups may be connected to another R group or to another atom of the drug-delivery molecule through alkyl, aryl, —O—, —S—, or —NR— where R is H, aryl or alkyl, or —C(O)—, provided there are no O—O, S—S, or S—NR bonds.

wherein m is 0-50;

wherein o is 0 or 1;

wherein J is —O—, —S—, or —NR—;

wherein R is H, alkyl or aryl;

wherein M is a masking group selected from the group consisting of —C(O)R, —C(O)OR, —C(O)NRR, —C(S)R, —C(S)OR, —C(O)SR, —C(S)NRR, —CRR(OR), —CR=CRR, —C(OR)=CRR, and —CR(OR)(OR);

wherein each R is, independently, as defined above, and wherein Y and Y' are, independently, reactivity-modifying groups selected from the group consisting of H, alkyl, aryl, —CN, —C(O)R, —C(O)OR, —C(O)NRR, —S(O)R, —S(O)$_2$R, —P(O)(OR)(OR), and —P(O)(OR)(NRR); and any of the foregoing groups attached to —U—[P];

wherein each R is, independently, as defined above;

wherein each E is, independently, H or a reactivity-modifying group selected from the group consisting of aryl, alkyl, —OR, —SR, —NRR, halide selected from F, Cl, Br and I, —CN, —C(O)R, —C(O)OR, —C(O)NRR, —S(O)R, —S(O)₂R, —P(O)(OR)(OR), and —P(O)(OR)(NRR); and adjacent E groups may be connected to each other to form a fused cycloalkyl or aromatic ring;
wherein each R is, independently, as defined above; and
provided that -J-M is ortho or para to the carbon to which A is attached; and
stereoisomers, pharmaceutical salts, and mixtures of the foregoing.

In one subclass of the foregoing molecules, A is selected from the group consisting of

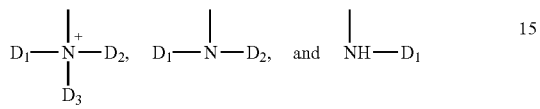

wherein $D_1$, $D_2$ and $D_3$ are substituents of amine drug molecules and

may be present as the corresponding ammonium salts.

The polymeric moiety is preferably as described above and, again, the polymeric moiety can be absent to give a prodrug in which the drug will not be active until the drug is released. Preferably the remainder of the prodrug is chosen such that after release of the drug, the remainder of the prodrug molecule is non-toxic.

A further class of drug-delivery molecules of this invention have a formula selected from the group consisting of:

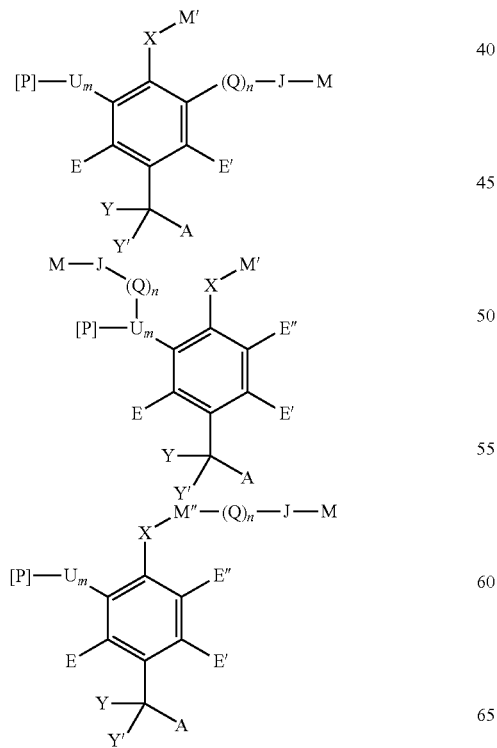

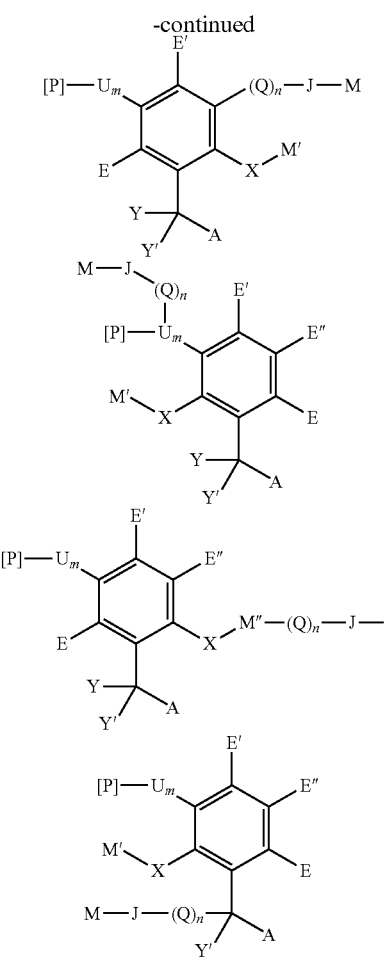

wherein A is a moiety selected from the group consisting of tertiary amine drug ion moieties, secondary amine drug moieties, primary amine drug moieties, alcohol drug moieties, and thiol drug moieties connected to the phenyl ring carbon through the amine nitrogen; alcohol oxygen, or thiol sulfur;

wherein [P] is a pharmaceutically acceptable polymeric moiety, optionally comprising repeats of the moiety depicted for the remainder of the drug-delivery molecule, said repeats comprising the drug molecule moiety and said repeats being spaced along said polymeric moiety;

wherein each U is, independently, selected from the group consisting of alkyl, aryl, and aralkyl moieties, —O—, —S—, —NR—, —C(O)—, —C(O)O—, —C(O)N(R)— and —O—P(O)(OR)—;

wherein each R is independently, H, alkyl, or aryl, and two R groups may be connected to another R group or to another atom of the drug-delivery molecule through alkyl, aryl, —O—, —S—, or —NR— wherein R is H, alkyl or aryl, or —C(O)—, provided there are no O—O, S—S or S—NR bonds;

wherein m is 0-50;

wherein X is —OR, —SR, or —NR—, wherein R is as defined above;

wherein M and M' are masking groups selected from the group consisting of —C(O)R, —C(O)OR, —C(O)NRR, —C(S)R, —C(S)OR, —C(O)SR, —C(S)NRR, —CRR(OR), —CR=CRR, and —C(OR)=RR;

wherein each R is, independently, as defined above;

wherein M" is selected from the group consisting of —C(O)—, —C(S)—, —C(NR)—, —P(O)(OR)—, —P(O)(NRR)—, —P(S)(OR)—, and —P(S)(NRR)—;
wherein each R is, independently, as defined above;
wherein Y and Y' are, independently, reactivity-modifying groups selected from the group consisting of H, alkyl, aryl, —CN, —C(O)R, —C(O)OR, —C(O)NRR, —S(O)R, —S(O)₂R, and —P(O)(OR)(OR), and —P(O)(OR)(NRR);
wherein each R is, independently, as defined above; and
wherein each of E, E' and E" is independently H or a reactivity-modifying group selected from the group consisting of aryl, alkyl, —OR, —NRR, halide selected from F, Cl, Br and I, —CN, —C(O)R, —C(O)OR, —C(O)NRR, —S(O)R, —S(O)₂R, and —P(O)(OR)(OR), and —P(O)(OR)(NRR); and adjacent E groups may be connected to each other to form a cycloalkyl or aromatic ring; and
wherein each R is, independently, as defined above; and
wherein each Q is, independently, a moiety selected from alkyl, aryl, or aralkyl moieties, —O—, —S—, —NR—, and —C(O)—, provided however that Q does not include O—O, S—S or S—NR bonds;
wherein R is as defined above;
wherein n is 1-6; and
wherein J is —OR, —SR—, or —NR—;
wherein R is as defined above; and
stereoisomers, pharmaceutical salts, and mixtures of the foregoing.

In a subclass of the foregoing molecules, A is selected from the group consisting of

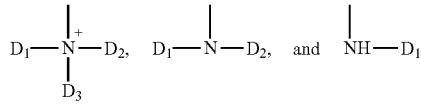

wherein $D_1$, $D_2$ and $D_3$ are substituents of amine drug molecules, and

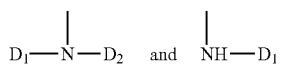

may be present as the corresponding ammonium salts.

The polymer moiety is preferably as set forth above, or the polymeric moiety may be absent, to give a prodrug in which the drug will no be active until released. Preferably, the remainder of the prodrug is chosen such that after release of the drug, the remainder of the prodrug molecule is non-toxic.

A drug-delivery molecule suitable for release of oxycodone via a fragmentation reaction involving a single masking group has the structure:

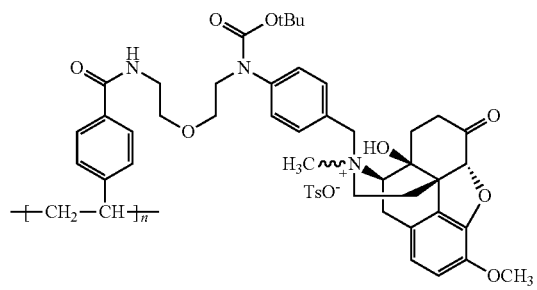

wherein n is about 10 to about 10,000.

A drug-delivery molecule suitable for release of oxycodone via a fragmentation reaction involving a two-stage unmasking has the structure:

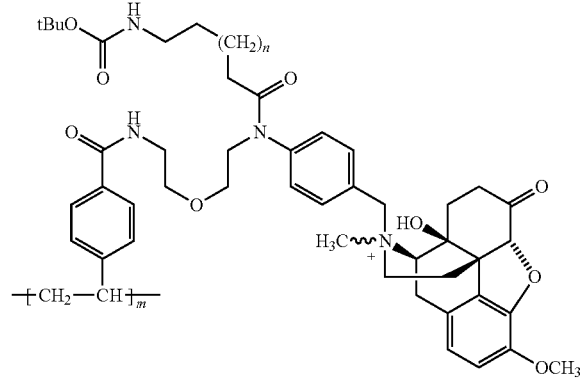

wherein n is 0-2 and m is about 10 to about 10,000.

A further class of drug-delivery molecules of this invention have formulas selected from the group consisting of:

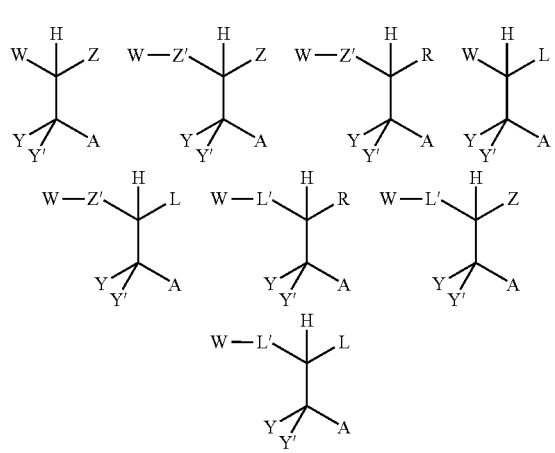

wherein A is a moiety selected from the group consisting of tertiary amine drug ion moieties, secondary amine drug moieties, primary amine drug moieties, alcohol drug moieties, and thiol drug moieties connected to the remainder of the molecule through the amine nitrogen, alcohol oxygen, or thiol sulfur;

wherein W is [P]-Um-;
wherein [P] is a pharmaceutically acceptable polymeric moiety, optionally comprising repeats of the moiety depicted for the remainder of the drug-delivery molecules, said repeats comprising the drug moiety, and said repeats being spaced along said polymeric moiety;
wherein each U is, independently, selected from the group consisting of alkyl, aryl, and aralkyl moieties, —O—, —S—, —NR—, —C(O)—, —C(O)O—, —C(O)N(R)— and —O—P(O)(OR)—;
wherein each R is, independently, H, alkyl or aryl; and two R groups may be connected to another R group or to another atom of the drug-delivery molecule through alkyl, aryl, —O—, —S—, or —NR— wherein R is H, aryl or alkyl, or -OC(O)—, provided there are no O—O, S—S, or S—NR bonds;
wherein m is 0 to 50;

wherein R shown in the structure above is H, aryl or alkyl, and two substituents of said R groups may be connected to another R group or to another atom of the drug-delivery molecule through alkyl, aryl, —O—, —S—, or —NR— wherein R is H, aryl or alkyl, or —C(O)—, provided there are no O—O, S—S, or S—NR bonds;

wherein Y and Y' are, independently, reactivity-modifying groups selected from the group consisting of H, alkyl, aryl, —CN, —C(O)R, —C(O)OR, —C(O)NRR, —S(O)R, —S(O)$_2$R, —P(O)(OR)(OR), and —P(O)(OR)(NRR), and Y or Y' may be any of the foregoing connected to [P]-Um-;

wherein each R is, independently, as defined above; and wherein Z is selected from the group consisting of —C(O)R, —C(O)OR, —C(O)NRR, —CN, —NO$_2$, —P(O)(OR)(OR), —P(O)(NRR), —S(O)R, —S(O)$_2$R, and aryl;

wherein each R is, independently, as defined above; and wherein Z' is selected from the group consisting of aryl, —C(O)—, —S(O)—, —S(O)$_2$—, —P(O)(OR), —P(O)R, and —P(O)(NRR)—;

wherein each R is, independently, as defined above; and wherein L is selected from the group consisting of —CR(OR)(OR), —C(OR)(OR)(OR), —C(OR)=CRR, —CR(OR)(SR), —CR(OR)(NRRR), —CR(NRR)(NRR), wherein each R is, independently, as defined above; and wherein L' is selected from the group consisting of —C(OR)(OR) and —C(OR)(SR)—;

wherein each R is, independently, as defined above; and stereoisomers, pharmaceutical salts, and mixtures of the foregoing.

In a subclass of the foregoing molecules, A is selected from the group consisting of

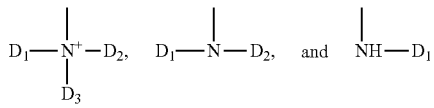

wherein $D_1$, $D_2$ and $D_3$ are substituents of amine drug molecules, and

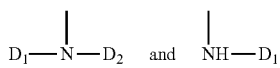

may be present as the corresponding ammonium salts.

The polymeric moiety is as set forth above, and again, may be replaced by a moiety of a smaller molecule which blocks activity of the drug until the drug is released.

A drug-delivery molecule useful for delivery of oxycodone via an elimination release reaction, having a masked electron withdrawing group has the following structure:

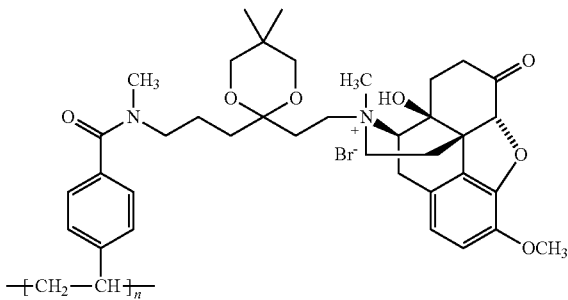

wherein n is about 10 to about 10,000

This invention also provides drug-delivery polymers comprising subunits having the formula:

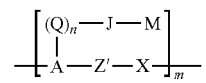

wherein J is —O—, —S—, or —NR—;
  wherein R is H, aryl or alkyl, and two R groups may be joined through aryl, alkyl, —O—, —S—, or —NR— where R is H, alkyl or aryl, or —C(O)—, provided there are no O—O, S—S or S—NR bonds;
  wherein m is 1 to about 1,000, about 10,000, or about 250,000.

wherein M is selected from the group consisting of —CRR(OR), —CR(OR)(OR), —C(O)R, —C(O)OR, —C(O)NRR, —C(OR)=CRR, —CR=CRR, —C(S)OR, —C(S)NRR, —C(S)R,
  wherein R is as defined above; and wherein each Q is, independently, aryl, alkyl, —O—, —S—, —NR—, or —C(O)—, wherein R is as defined above;

wherein n is 0-7, wherein Z' is —C(O)—, —C(S)—, —P(O)(OR)—, or —P(O)(NRR),
  wherein each R is, independently, as defined above; and wherein X is —O—, —S—, or —NR—;
  wherein R is as defined above; and wherein A is —NR—, alkyl or aryl,
  wherein R is as defined above.

The polymer may comprise polymeric monomers, e.g. up to about 1,000, polymeric monomers of a pharmaceutically-acceptable polymer between the subunits or repeats of said subunits.

The polymeric monomers may be any known to the art, including without limitation, monomers of biodegradable and non-biodegradable polymers selected from the group consisting of polystyrene, polyamine, polybutadiene, polymethacrylate, polyethylene, polyacrylate, polyamide, 1,3-dienes, methylcellulose, polyamino acids and polysaccharides, polyglycolate and polylactate, and alkyl and aryl-substituted derivatives thereof, and copolymers of any of the foregoing. In a specific embodiment, the monomers are —C(R)(R))C(R)(R)— wherein each R is, independently, H, aryl or alkyl. Preferably for every thousand conventional monomer units, the chain has about 1 to about 100 degradable polymer subunits of this invention.

One embodiment of the drug-delivery polymers of this invention provides a drug-delivery polymer comprising the foregoing subunits of this invention used to crosslink polymer chains made up of other polymeric monomers.

Specific drug-release polymers of this invention have formulas selected from the group consisting of:

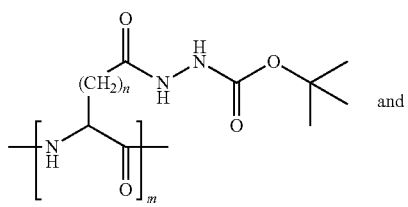

and

-continued

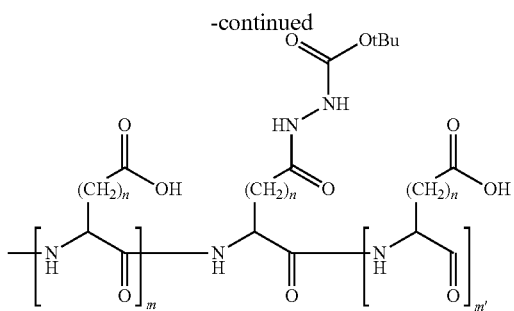

where n is 1-2 and m and m' are 0 to about 1,000.

This invention also provides an enamine drug-delivery molecule having the formula:

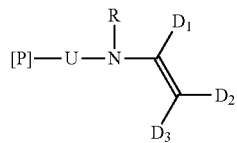

wherein [P] is a pharmaceutically acceptable polymeric moiety, optionally comprising repeats of the moiety depicted for the remainder of the drug-delivery molecules, said repeats comprising the drug moiety, and said repeats being spaced along said polymeric moiety;

wherein each U is, independently, selected from the group consisting of alkyl, aryl, and aralkyl moieties, —O—, —S—, —NR—, —C(O)—, —C(O)O—, —C(O)N(R)— and —O—P(O)(OR)—;

wherein each R is, independently, H, alkyl or aryl; and two R groups may be connected to another R group or to another atom of the drug-delivery molecule through alkyl, aryl, —O—, —S—, or —NR— where R is H, alkyl or aryl, or —C(O)—, provided there are no O—O, S—S, or S—NR bonds;

wherein m is 0 to 50; and $D_1$-$D_3$ are substituents on the drug, and one or two of $D_1$-$D_3$ may be H.

A specific enamine drug-delivery molecule has the formula:

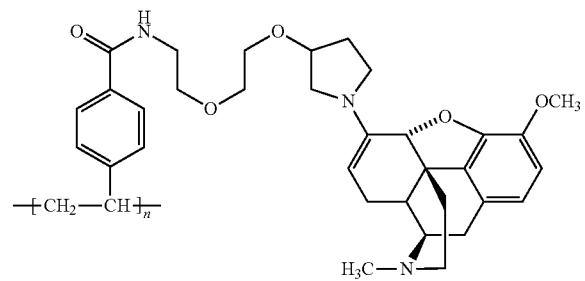

wherein n is about 10 to about 10,000.

Controlling the Rate of Drug Delivery.

One of the most attractive features of this invention is that it is possible to control the rate of delivery of a drug in a predictable fashion. This may be done by controlling the rate of the unmasking reaction, controlling the rate of the release reaction, or by controlling both of the rates. In addition, drug-delivery compositions can be prepared using mixtures of drug-delivery molecules of this invention, each having selected release rates, the amount of each type of molecule being calculated to provide a predictable, selected release rate for the composition as a whole.

i) Controlling the Rate of the Unmasking Reaction.

Use of the unmasking reaction to control the overall rate of drug delivery presupposes that this step is slow (or comparable) in rate to the release reaction. In the extreme case, the release reaction is very fast, and the unmasking reaction becomes rate controlling. Controlling the rate of the unmasking reaction may be accomplished by changing the nature of the protecting group (the masking group) which masks the triggering functional group. In the example given in Scheme 1, the masking group is an ethoxyethyl group. If, instead, an ethoxymethyl (or other alkoxymethyl) group were employed, the rate of the unmasking reaction would become markedly slower. A more subtle means to slow the rate of the unmasking reaction would be to employ an ethoxyethyl group that incorporated electron-withdrawing substituents near to the acetal carbon, e.g., $ROCH(OEt)CH_2X$, $ROCH(OEt)CHX_2$ or $ROCH(OEt)CX_3$, where X is an electron-withdrawing group and R represents the remainder of the drug delivery composition. Alternatively, this more subtle level of slowing the rate of unmasking can be accomplished by the use of cyclic acetals; for example, the triggering alcohol can be masked as a tetrahydropyranyl (THP) ether. If it should be desired to speed up the rate of the unmasking reaction, a derivative that is more sensitive to hydrolysis can be employed. Thus, instead of making a derivative of the triggering alcohol ROH as $ROCH(OEt)CH_3$, one can make it $ROC(OEt)R'R''$ (for example, the commonly used $ROC(OEt)(CH_3)_2$), in which R' and R'' are alkyl or aryl or substituted alkyl or aryl, such groups and their substituents being chosen to appropriately vary their electron-donating or withdrawing properties with respect to the acetal/ketal carbon. The triggering alcohol group may also be masked as an ester, carbonate, carbamate, or hemiaminal. Examples of some of the means by which the triggering alcohol may be masked are illustrated in Scheme 2. The only masking group amongst those shown that is not a standard protecting group for alcohols is the epoxide; this represents a novel method for masking what will become the triggering alcohol group, as the alcohol is produced as a consequence of an acid catalyzed epoxide opening under the acidic aqueous environment of the stomach. The groups R, R', R'', R''' may be chosen to enhance or decrease the rate of this opening.

Scheme 2

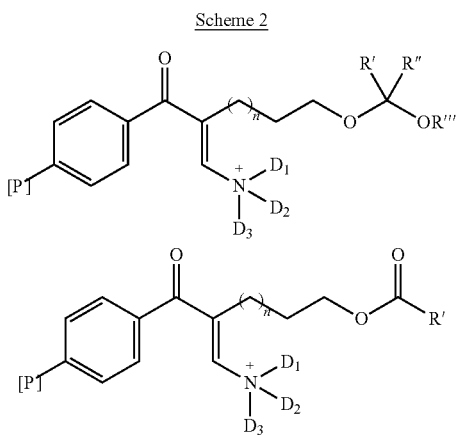

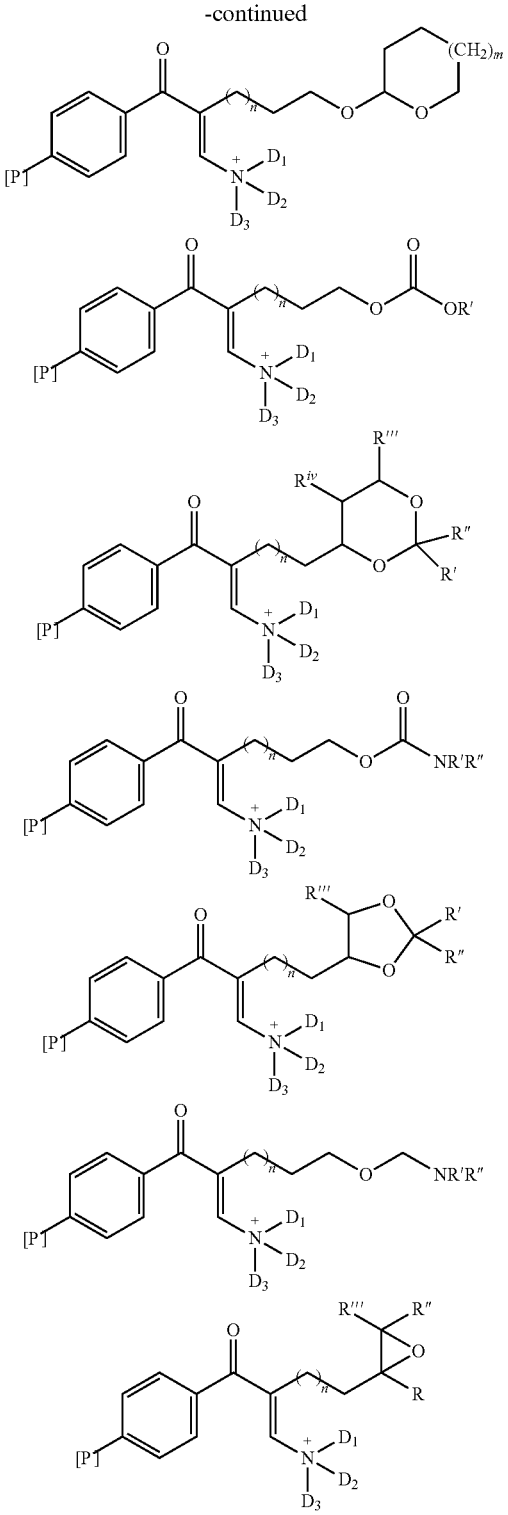

note: epoxide opens to vicinal diol under acidic aqueous conditions
$ND_1D_2D_3$ represents the drug to be released. "n" is zero, one, two, three, etc. "m" is independently zero, one, two, three. R', R", R''', $R^{iv}$ are independently H, alkyl substituted alkyl, aryl, substituted aryl. [P] represents the polymer.

Though the focus of the above discussion has been on the use of masking groups that are removed under the acidic conditions of the stomach, it may sometimes be desirable to employ masking groups that are removed under mildly or strongly basic conditions. Examples of such groups that can mask alcohols are esters, carbonates and carbamates. Epoxides may be employed for this purpose, serving as masked diols by undergoing base hydrolysis. It may also be desirable at times to utilize masking groups that are removed under both acidic and basic conditions. Such groups include anhydrides, imides, epoxides, and esters. In some circumstances it may be possible to make do without the masking group altogether, provided that the drug delivery composition can be maintained in a substantially dry form. Under dry conditions, intramolecular reaction will not take place; introduction into an aqueous environment will then allow the release reaction to occur.

Controlling the Rate of the Release Reaction

Although the unmasking reaction may, in some circumstances, be used to control the rate of drug delivery, it will generally be more desirable to control the rate using the release reaction. There are two reasons for this. Firstly, in many cases it will be desirable to have drug delivery occur over a fairly long period. If the rate of the delivery is controlled by an acid-mediated unmasking reaction this could cause difficulties in the slow release of a drug, since the delivery composition will inevitably be moved out of the acidic environment of the stomach into the less acidic intestinal tract, where the rate of the unmasking reaction will then slow. Secondly, the acidity of individuals' stomachs may be expected to vary, causing a corresponding variation in the rate of the unmasking reaction. This would lead to an undesirable level of variability in the rate of drug delivery in differing individuals. Having a rapid unmasking reaction, followed by a controlled rate of release reaction, is much more desirable; differing stomach acidities will no longer cause variations in the delivery rate, and drug delivery can continue as the unmasked drug makes its way through the intestinal tract.

The conceptual basis for how to accomplish the variation of the rate of the release reaction in the preferred embodiment of the invention described above is the same as that responsible for the success of the controlled release strategy in the first place; the reason why the unmasked triggering alcohol that is capable of reacting intramolecularly is so much more effective than the water and/or other nucleophiles present in the stomach and intestinal tract. In an attempt to understand how it is that enzymes catalyze chemical reactions at such a high rate, chemists have studied the effect of propinquity on chemical reactions: the effect of localizing two reactants in enforced, close proximity to one another. In studying reactions of this type (typically intramolecular reactions), chemists have arrived at a measure of this effect, termed the "effective molarity," which is defined as the molarity that two unconnected intermolecular reactants would have to be present at in order to achieve the same rate of reaction as the intramolecular reaction being examined. Effective molarities can be almost unimaginably, unrealistically high; much higher than would be physically possible in an actual bimolecular reaction. Thus, the effective molarity of the carboxylate oxygen in the lactonization of 3-(2-hydroxyphenyl)propanoic acid to form a 6-membered ring is reported to be 470,000 M, a value unattainable in a real solution. These amazingly high effective molarities are a consequence of reduced entropic requirements for intramolecular reactions; in a simple sense, one can say that the two reactants are unable to avoid each other, and are therefore much more liable to react tan if they were not both present on the same molecule. It is for this reason that the triggering hydroxyl group in the preferred embodiment of the invention described above can act so much more effectively than external nucleophiles.

The same factors that are known to influence effective molarities can be used to adjust the rate of the release reaction. Ring size can play a very substantial role in influencing the rates of intramolecular reaction and effective molarities. For example, in the cyclization of a hoMologous series of terminal bromoalkylcarboxylic acids, it was found that formation of a 5-membered ring lactone product occurred more than 1000-fold more rapidly than formation of the corresponding 6-membered ring compound, while formation of the 7-membered ring product was 270-fold slower. Formation of larger rings was even slower. Thus, in the context of the preferred embodiment of the invention described in Example 1, utilization of γ-butyrolactone, having no $(CH_2)_n$ spacer, in place of δ-valerolactone, having one $(CH_2)_n$ spacer would lead to a drug delivery composition that would give a much more rapid rate of drug release, since the effective molarity for the formation of a 5-membered ring is much higher than that of the 6-membered ring. Conversely, utilization of ε-caprolactone, having two $(CH_2)_n$ spacers, gives a drug delivery composition that provides oxycodone much more slowly, due to formation of a final 7-membered ring product.

More subtle effects in rates are also possible. Addition of alkyl or aryl groups to the chain connecting the two reactive portions of a molecule will generally cause increases in rates of intramolecular reactions. For example, arbitrarily defining the rate of the intramolecularly-catalyzed hydrolysis of N-phenylsuccinamic acid as 1.0, addition of an α-methyl group on the succinate increases the rate by a factor of 2, addition of two α-methyl groups increase the rate by a factor of about 12, while the α,α,β-trimethyl compound reacts 350 times faster. Larger substituents typically have larger effects. Even more dramatic rate effects with substitution patterns have been seen in more rigid aromatic systems. Thus, the rate of the release reaction can be controlled in a fairly crude fashion by constructing a drug delivery composition with substituents which will form a ring of an appropriate size during the intramolecular release reaction, which can then be "fine-tuned" by placing one or more substituents of appropriate sizes on the chain connecting the two reactive portions of the molecule (the triggering functional group and the reactive vinylic carbon). Some examples of this method for controlling release rate for a given intramolecular ring size are shown in Scheme 3.

Scheme 3
Delivery rates as a function of added substitutents. Substituents may be placed in other locations to modify rates, and sized of sunstituents may also influence rates.

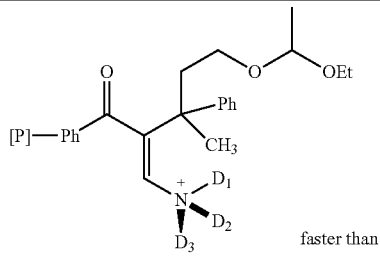

faster than

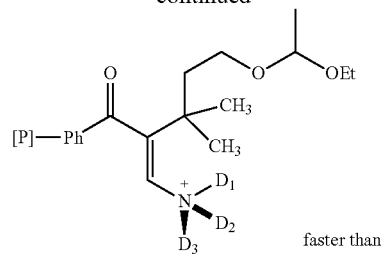

faster than

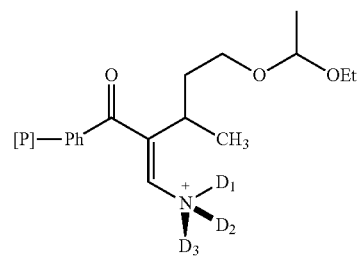

The rate of the release reaction may also be controlled by modifying the nature of the nucleophilic triggering atom. For example, steric hindrance in the vicinity of the nucleophilic atom may slow the reaction. More importantly, modifications to the basicity of the nucleophilic atom may play a large role in varying the rate. The most dramatic effects are expected to be seen in the case of changing the atom type of the triggering functional group.

For example, using an amine as a nucleophilic triggering group produces very large increases in the rate of the release reaction compared to use of —O— or —S— as the nucleophilic triggering group, especially if care is taken to ensure that the basicity of the amine is such that it is not completely protonated under the reaction conditions (e.g., through use of the nitrogen of a substituted aniline as the nucleophile, as in Scheme 4).

Scheme 4
Modified delivery rates through the use of modified nuclephilic triggering atoms

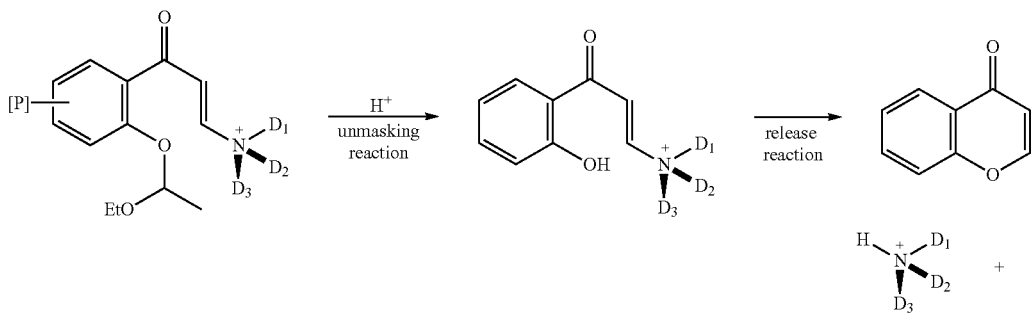

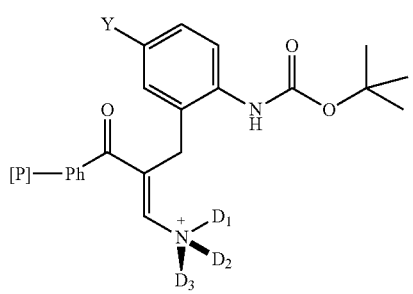
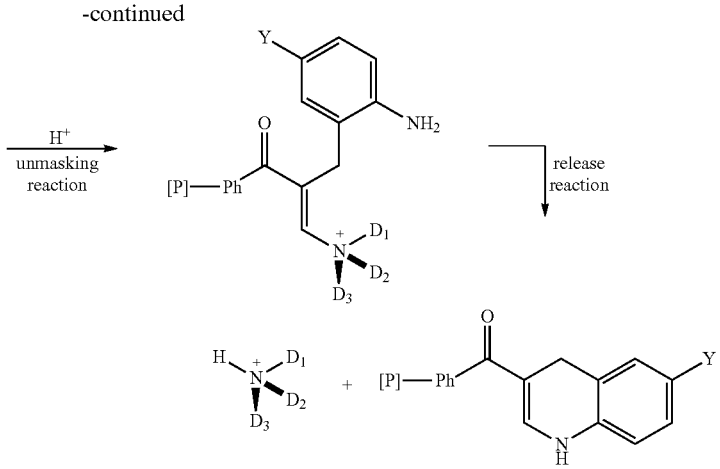

Y = H or substituent that modifies basicity of nucleophilic amine. Carbamate masking group shown; other masking groups possible.

Further Control Over Drug Delivery Rates.

Two general methods can be used to attain greater control over delivery rates of drugs: use of both the unmasking and the release reaction rates, and use of multiple drug delivery compositions. For the former strategy to work, the rates of the unmasking and the release reactions must be fairly similar; otherwise, one will be rate limiting, and control the overall rate of release. In the second strategy, one or more drug delivery compositions are employed; i.e., a drug-delivery composition that has a short half-life may be employed in conjunction with a second having a longer half-life, or even a third. In this way it should be possible to finely tune the delivery profile of the drug. The combination of drug delivery compositions may be done either at a crude physical level by mixing together the separately-prepared drug-delivery polymers, or may be done at a molecular level by using polymers that have a mixture of drug delivery compositions incorporated therein.

Controlled Release Molecules Based on Fragmentation Reactions.

Benzylic amines, ethers and thiols having a strong electron donating group in an ortho or para relationship relative to the benzylic carbon are known to undergo fragmentation reactions in which an amine, alcohol or thiol is released, and a transient quinone type structure is formed from the aromatic ring; the latter then reacts with an external nucleophile to regenerate the aromatic system. This fragmentation can serve as the basis for a controlled release drug delivery molecule by use of masking groups on donor atoms that are substituents on aromatic rings. When masked, the donor atom is a much less strong donor; when the mask is removed, the full donor ability returns, leading to a fragmentation reaction and release of the drug. These strategies are illustrated for an oxygen donor atom in Scheme 5. Though only an ethoxyethyl group is shown as a masking group, it is clear that any of the strategies discussed above, and illustrated in Scheme 5, could be used for this purpose.

Scheme 5

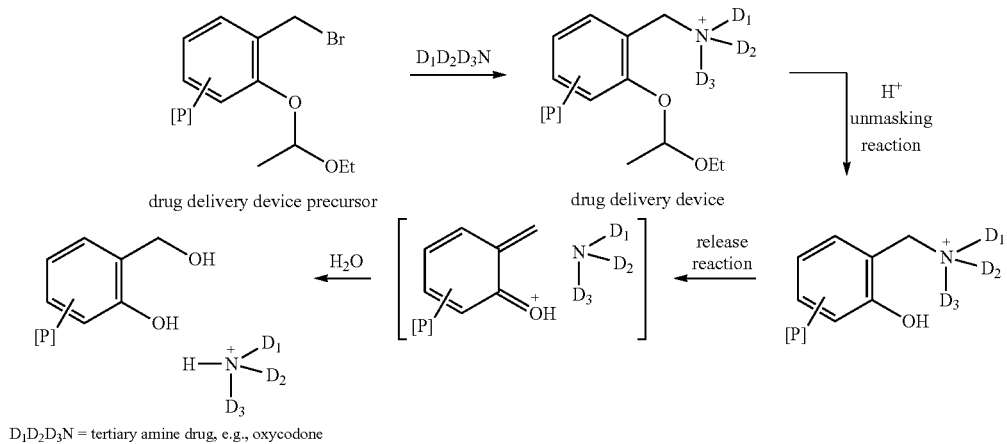

$D_1D_2D_3N$ = tertiary amine drug, e.g., oxycodone

The release of a drug from o- and p-aminobenzylammonium compounds is much more facile than that in the corresponding hydroxy compounds discussed above, due to the greater donating ability of nitrogen vs. oxygen. This strategy requires the use of masking groups sufficiently electron-withdrawing to inhibit the release reaction; once the amine is unmasked, release may be relatively rapid. This strategy, illustrated for a carbamate masking group, is shown in Scheme 6. Other potential masking groups for the amine include enamine and imine derivatives, as well as labile amides, or amides cleavable by enzymes present in the body.

Scheme 6

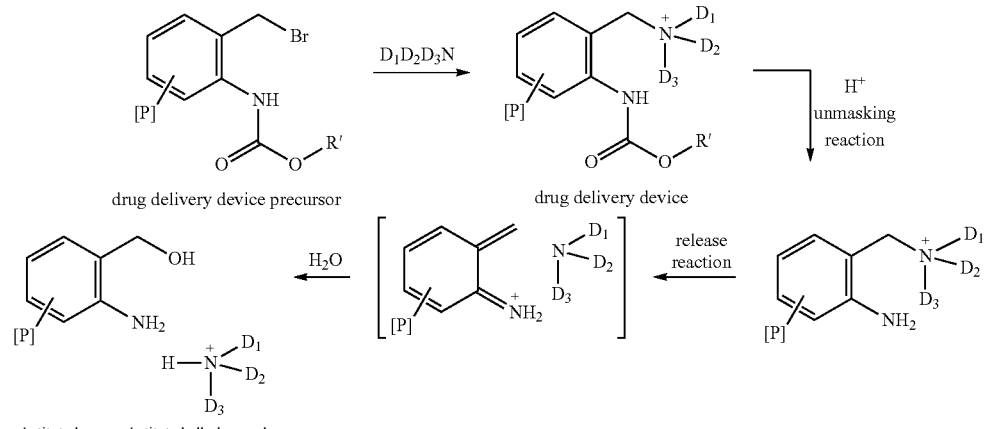

R = substituted or unsubstituted alkyl or aryl

The strategy for drug delivery just described utilizes simple masking groups—masking groups that are hydrolyzed in solution to directly expose an electron-donor atom that promotes fragmentation and release of the drug.

When the rate of the release reaction from the unmasked controlled release molecule is fast, and a satisfactory rate of the unmasking reaction cannot be attained, it may be desirable to utilize a two-stage unmasking sequence.

The two-stage unmasking group variants of this invention bear a close conceptual relationship to the drug-release compositions that rely on nucleophilic vinylic substitution reactions in the following sense. One adjusts the system (varying substituents as necessary) so that the fragmentation reaction is fast. Then, one incorporates a two-stage masking group, in which a second nucleophilic atom is masked by a second masking group, and is attached near to the first, or primary masking group that is decreasing the electron-donating ability of the donor atom. Removal of the second masking group provides the free second nucleophilic atom, which then reacts intramolecularly to remove the first, or primary masking group, thereby providing the active donor atom which facilitates fragmentation and release of the drug. One can then control the overall rate of release by controlling how fast the first masking group is removed; this can be done by the same type of intramolecular gross and fine tuning (adjusting the length and substituents of the spacers as described above.

The action of the two-stage unmasking variants of this invention is illustrated in Scheme 7 for the case in which the donor atom is a nitrogen, the first masking group is an amide, the nucleophilic atom is a nitrogen, the secondary masking group is a tert-butoxycarbamate (Boc), and there are four to six atoms between the nucleophilic atom and the carbon to which the drug is attached. The operation of the molecule is illustrated for a tertiary amine drug. When the controlled release polymer is exposed to the acidic environment of the stomach, the secondary masking group is removed to give the nucleophilic amine. This reacts with the amide carbonyl of the first, or primary masking group to provide the aromatic amine donor, which leads to fragmentation and release of the drug.

Scheme 7

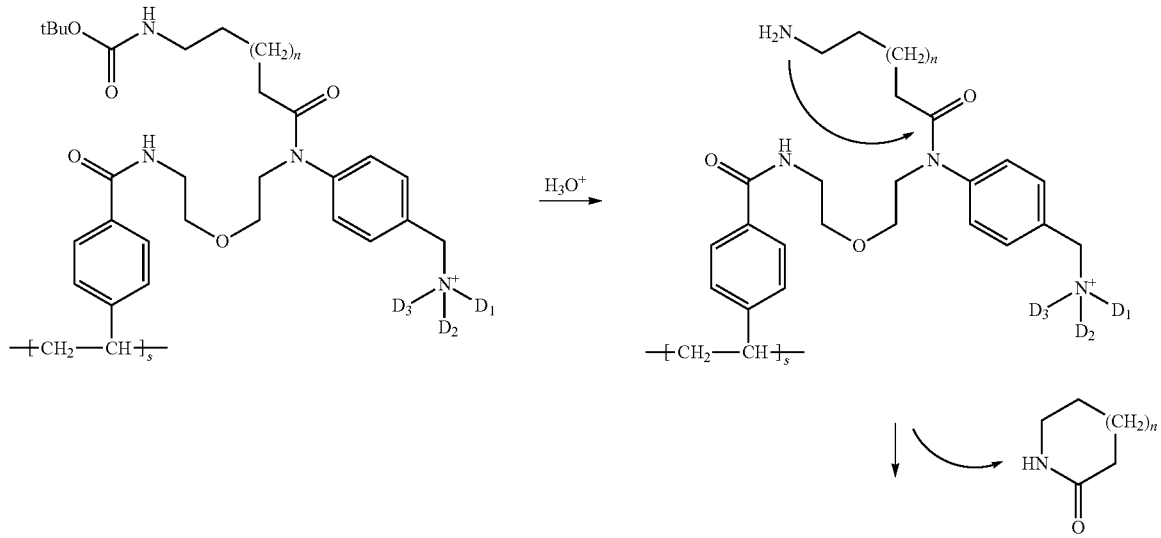

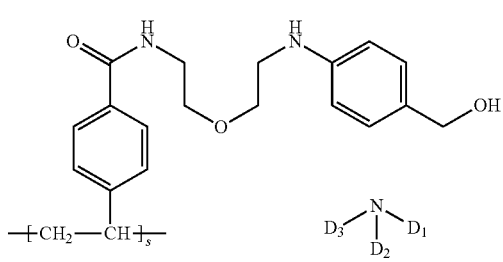
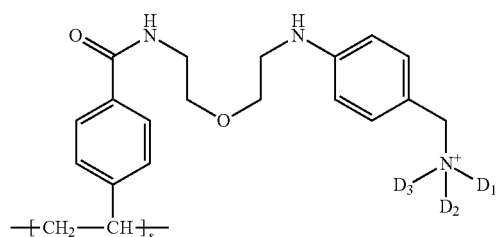

Though a single example of this sequential unmasking reaction is shown, the same principles discussed above for intramolecular reactions in release reactions of quaternary vinylammonium compounds applies here, allowing a finer degree of control over drug delivery. Thus, variation in the chain length between the nucleophilic amine and the masking group on the aromatic amine will affect the rate, as will the addition of substituents on the chain. Of course, replacement of the nucleophilic amine by an appropriately protected alcohol would provide a drug delivery system that operated more slowly. Similarly, any of the strategies illustrated in Scheme 2 can be used for the initial masking of the hydroxyl group.

Controlled Release Molecules Based on Elimination Reactions.

In a further embodiment of this invention, a drug that incorporates in its structure a tertiary, secondary or primary amine, or an alcohol or thiol, is covalently attached to a carbon, for example as shown below:

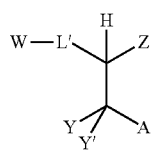

wherein W is [P]-Um- as defined above.

On the adjacent carbon to attachment point for the drug molecule moiety is a second carbon that has at least one hydrogen and at least one group capable of stabilizing a negative charge (an electron-withdrawing group, Z). In the simplest embodiment, exposure to the slightly basic environment of the intestine leads to loss of the hydrogen on the carbon bearing the Z group; in turn, this leads to an elimination reaction to give the free drug. In a slightly more complicated version of the molecule, the Z group is replaced by a group L' which is not an anion stabilizing group. However, exposure to acidic conditions transforms this group into an anion stabilizing group, thereby facilitating the elimination process. The rate of release in these compositions will be more dependent on the location in the body than previously-described embodiments, that is, the rate of release will show a greater pH dependence.

Controlled Release from Enamine Adducts of Drugs Incorporating Ketone Moieties.

Another embodiment of this invention comprises a drug-delivery molecule of a structure as shown below, which can be hydrolyzed as shown to release a ketone or aldehyde:

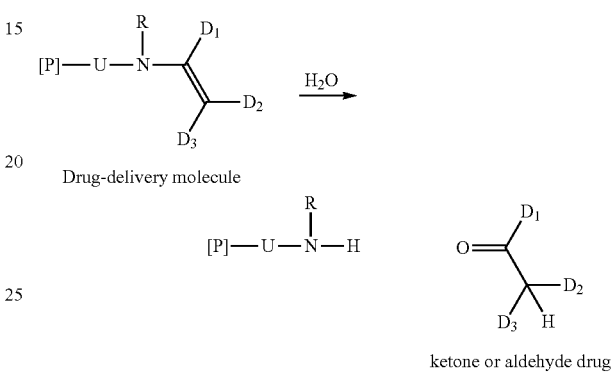

Drug-delivery molecule ketone or aldehyde drug wherein [P] is a pharmaceutically acceptable polymeric moiety, optionally comprising repeats of the moiety depicted for the remainder of the drug-delivery molecules, said repeats comprising the drug moiety, and said repeats being spaced along said polymeric moiety;

wherein each U is, independently, selected from the group consisting of alkyl, aryl, and aralkyl moieties, —O—, —S—, —NR—, —C(O)—, —C(O)O—, —C(O)N(R)— and —O—P(O)(OR)—;

wherein each R is, independently, H, alkyl or aryl; and two R groups may be connected to another R group or to another atom of the drug-delivery molecule through alkyl, aryl, —O—, —S—, or —NR— where R is H, aryl, or alkyl, or —C(O)—, provided there are no O—O, S—S, or S—NR bonds;

wherein m is 0 to 50; and $D_1$-$D_3$ are substituents on the drug, and one or two of $D_1$-$D_3$ may be H.

In this embodiment, the rate of release of the drug will be affected by the nature of the substituents (steric and electronic) on the nitrogen of the enamine, and by whether or not the nitrogen is part of a ring structure.

The polymer moiety is preferably as set forth above, or the polymeric moiety may be absent, to give a prodrug in which the drug will no be active until released. Preferably, the remainder of the prodrug is chosen such that after release of the drug, the remainder of the prodrug molecule is non-toxic.

Drug Delivery by Incorporation of Degradable Polymer Units into Polymers.

Another embodiment of this invention provides controlled release by use of polymer degradation. This allows release of native drugs; that is, the drugs have not been modified in any way, so they are not classified by the FDA as new drugs. In previously-described compositions, the drug is physically attached to a polymer that incorporates a nucleophile with a masking group; exposure to the acidic environment of the stomach unmasks the nucleophile, which then cleaves off the drug through an intramolecular reaction, the rate of which is controllable by ring size, choice of nucleophile, substituents, etc. In the present embodiment, the drug is not physically attached to the polymer, but is embedded or encapsulated in it. The polymer incorporates nucleophiles with masking groups. Exposure to selected conditions in the body unmasks the nucleophile, which then cleaves a bond of the polymer, thereby breaking the chain. This makes the polymer more permeable, allowing release of the drug. Once the masking group is gone, the rate of polymer degradation (and thus drug delivery) is largely independent of the environment. When the unmasking occurs in the stomach, the subsequent release occurs at a predictable rate in the intestine, and this release is controllable by the rate of an intramolecular reaction (or by the rate of the unmasking reaction).

These polymers can be used for any drug.

Polymers made up entirely of degradable polymer units may be used in this embodiment for embedding or encapsulating drugs. The polymers have the following structure:

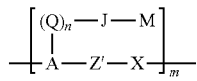

wherein J is —O—, —S—, or —NR—;
  wherein R is H, aryl or alkyl, and two R groups may be joined through aryl, alkyl, —O—, —S—, or —NR—, where R is H, alkyl or aryl, or —C(O)—, provided there are no O—O, S—S or S—NR bonds;
wherein m is 1 to about 10,000;
wherein M is selected from the group consisting of —CRR (OR), —CR(OR)(OR), —C(O)R, —C(O)OR, —C(O)NRR, —C(OR)=CRR, —CR=CRR, —C(S)OR, —C(S)NRR, —C(S)R,
  wherein R is as defined above; and
wherein each Q is, independently, aryl, alkyl, —O—, —S—, —NR—, or —C(O)—, wherein R is as defined above;
wherein n is 0-7,
wherein Z' is —C(O)—, —C(S)—, —P(O)(OR)—, or —P(O)(NRR),
  wherein each R is, independently, as defined above; and
wherein X is —O—, —S—, or —NR—;
  wherein R is as defined above; and
wherein A is —NR—, alkyl or aryl,
  wherein R is as defined above.

The polymer is used to coat a drug or encapsulate or embed it. It degrades as follows to release the drug:

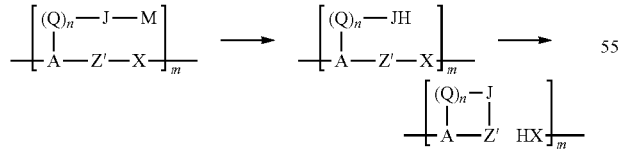

Polymers having non-degradable polymer units and also incorporating degradable polymer units may also be used in this embodiment.

In this case, a polymer containing non-degradable repeating monomer subunits or repeating monomer subunits that degrade more slowly than the degradable polymer subunits of this invention will contain a number of degradable polymer subunits of this invention. Preferably for every thousand conventional monomer units, the chain has about 1 to about 100 degradable polymer subunits of this invention. The polymer may or may not be crosslinked. The polymer may also have a formula as follows:

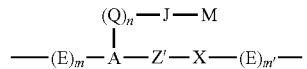

wherein Q, J, M, A, Z' n, m, and m' and X are as defined for the polymeric subunit described above; and wherein E is a repeating monomer unit of a polymer which may be polystyrene, polyamine, polybutadiene, polymethacrylate, polyethylene, polyacrylate, polyamide, 1,3-dienes, methylcellulose, polyamino acids and polysaccharides, and alkyl and aryl-substituted derivatives thereof, and copolymers of any of the foregoing. Most commonly E is a repeating unit, —C(R)(R')C(R")(R''')—, where R, R', R" and R''' are as defined above for R; and m and m' are independently about 1 to about 10,000.

This polymer degrades as follows:

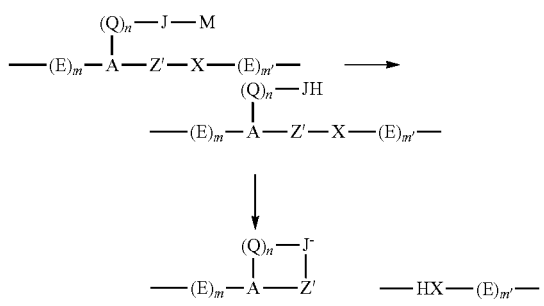

Polymers incorporating a degradable polymer subunit as a crosslinking agent may also be used in this embodiment.

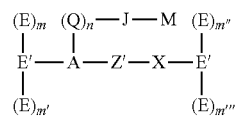

wherein Q, J, M, A, Z' n, m, E and X are as defined for the polymeric subunit described above;

m', m" and m''' are, independently, m; and

E' is defined as E, but is attached to the degradable polymer subunit.

This polymer degrades as follows:

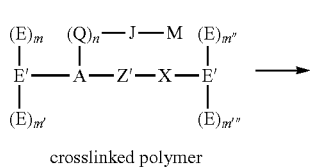

crosslinked polymer

-continued

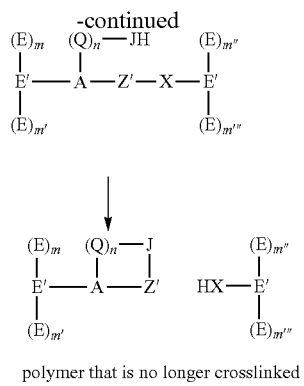

polymer that is no longer crosslinked

In this case, two polymer chains are attached together by a crosslinking agent that is degradable. Removal of the masking group leads to a non-crosslinked polymer, which is more permeable than the cross-linked polymer and thereby releases drugs more readily.

A similar strategy can be applied to making vesicles more permeable. Vesicles are formed from double chain surfactants, while single-chain surfactants form micelles. By tying together two single-chain surfactants with a potentially labile linkage that can be cleaved intramolecularly by an unmasked triggering functional group, one forms a double-chain surfactant that can be used to form vesicles. Exposure to an acidic environment causes unmasking of a triggering group that then intramolecularly cleaves the linkage between the two surfactant chains, converting them into a pair of single-chain surfactants that then makes the vesicle more permeable to diffusion and may even lead to breakdown of the vesicle. The vesicle does not have to be made up completely of these cleavable double-chain surfactants. By varying the proportion of the cleavable double-chain surfactants with appropriate non-cleavable double chain surfactants it is possible to control the rate and the extent of vesicle permeability and/or breakdown.

EXAMPLES

Those skilled in the art recognize that in most cases reactions of compounds attached to polymers are best carried out using large excesses of reagents, followed by washing away excess reagent. This generalization does not hold true in all cases, however; in some instances it may be the case that there are two functional groups present in the polymer-supported molecule that are capable of reacting with an added reagent, given sufficient time or excess or reagent. In those cases, it may be important to limit the amount of reagent to a slight excess over that theoretically required, or to conduct the reaction in the mildest possible fashion to achieve reaction of the more reactive of the two functional groups. Since it is not possible to purify a polymer-supported molecule, control of the amount of reagent employed in such reactions requiring discrimination between functional groups relies on an estimate of the molar amount of the target functional group. Absent highly sophisticated analytical techniques this molar amount is best estimated by careful drying and subsequent weighing of the polymer at each step of a sequence, thereby allowing an estimate of the yield of each reaction.

Since yields in these reactions may depend on the particular batch and characteristics of the starting polymer employed, as well as on variables such as mixing, shaking or stirring rate (which typically should be slow, and gentle to avoid physical damage to the polymer), as well as the ambient temperature, what is given below are general descriptions of representative preparations of the controlled release devices. The stoichiometry of reactions in which some care is required should be based on the estimates of available functional group obtained by weighing data. Those familiar with the art are aware that the times and temperatures given for reactions may not be critical, and that variations in these parameters may often, but not always be employed without decreases in yield.

Laboratory scale separation of the polymer-supported molecules from excess reagent is carried out by transferring the polymer and any solution to one or more centrifuge tubes, centrifuging, and then removing the supernatant liquid. Roughly three to five volumes (relative to the polymer volume) of an appropriate wash solvent is added and the contents are throughly, but gently mixed. Centrifugation is followed by removal of the supernatant. This procedure is repeated until an analytical technique appropriate for the reagent or side-product in question shows its absence. This centrifugation technique may be replaced in many instances by filtration through an appropriate device.

Example 1

Preparation of a Polymeric Precursor for Drug Delivery Compositions Utilizing a Vinylically-Bound Drug and an Acetal Masked Oxygen Triggering Atom Scheme 8 shows preparation and operation of a drug delivery composition that utilizes a masked oxygen triggering atom, using fentanyl as the example drug.

Reaction of the known macroreticular polymer poly(4-bromostyrene) with 1.1 molar equivalent of n-butyl lithium in dry THF at −78° C. for one hour, accompanied by gentle agitation or swirling, is followed by addition of 1.1 molar equivalent of δ-valerolactone (8b, n=1 in Scheme 8) as a solution in dry THF. (In Scheme 8, the symbol ( )$_n$ indicates $(CH_2)_n$.) After warming to room temperature, slightly greater than two molar equivalents of 1-ethoxyethene is added, followed by 1.2 molar equivalents p-toluenesulfonic acid. The resulting alcohol protected ketone is then washed with 10% sodium methoxide in absolute methanol and then methanol to remove excess reagents and salts. This is followed by washing with dichloromethane to remove methanol, drying, and weighing to estimate the reaction yield. The polymer is covered with 3-4 volumes of ethyl formate, and 4 molar equivalents of tetrabutylammonium hydroxide is added. The mixture is swirled twelve hours with an orbital shaker, then washed to neutrality with absolute ethanol, and washed again with ethanol-free chloroform to remove ethanol. Two molar equivalents p-toluenesulfonyl chloride is then added, and the mixture swirled for 24 hours with an orbital shaker. The resulting polymeric vinyl tosylate is washed with absolute ethanol to remove any excess p-toluenesulfonyl chloride and salts. The resulting resin constitutes the precursor of the fentanyl delivery composition. This same resin may be used for the delivery of other drugs that possess a nucleophilic tertiary amine. A more active resin may be prepared by use of trifluoromethanesulfonic anhydride in place of the p-toluenesulfonyol chloride. One familiar with the art will recognize that the above procedure may be applied without essential change with gamma-butyrolactone or caprolactone to provide delivery devices that will deliver drug at altered rates.

Scheme 8
Preparation of the Drug Delivery Device

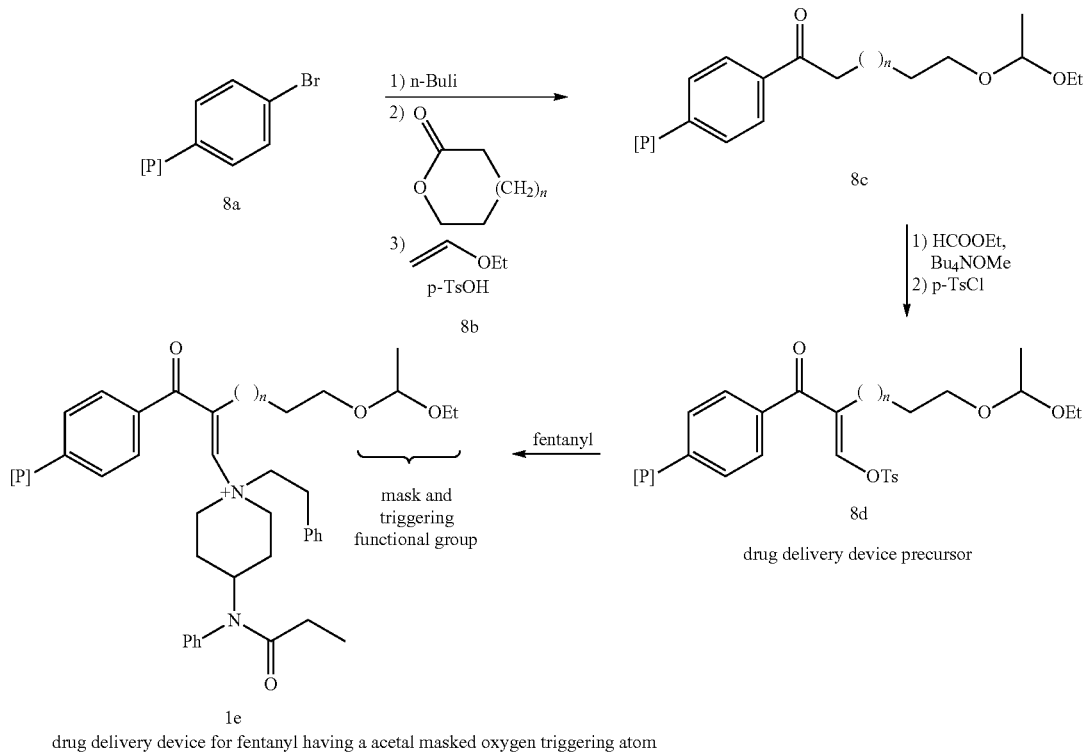

drug delivery device for fentanyl having a acetal masked oxygen triggering atom

Example 2

Formation of an Vinylically-Bound Fentanyl Delivery Composition Having an Acetal Masked Oxygen Triggering Atom The precursor resin prepared above (tosylate or triflate) is treated with a saturated solution of fentanyl in chloroform and heated at about 40° with swirling for a sufficient time to allow formation of the vinylammonium salt of fentanyl. When reaction is complete, the Fentanyl Drug Delivery Composition is centrifuged and the solid washed to recover unreacted fentanyl, which may be recycled. Those familiar with the art recognize that different drugs may require somewhat different conditions to accomplish the displacement of the sulfonate group by the drug. Triflates will generally react more readily than tosylates, and the use of alternative polar solvents may be desirable (e.g., DMF, nitromethane, or in some cases alcohol solvents). In particularly difficult substrates, the use of more elevated temperatures may be employed, provided that conditions are chosen such that loss of the masking group does not occur (e.g., no acidic substrates or solvents) The use of high pressure (>5 kbar) may also facilitate the reaction. It is also clear to those familiar with the art that drugs incorporating secondary amines and primary amines will generally react with greater ease to form the corresponding drug delivery composition. It is also clear that drugs incorporating an alcohol or thiol will react with the drug delivery composition precursor, preferably in the presence of a hindered or otherwise non-nucleophilic base, to give the corresponding drug delivery composition. Reactions of drugs incorporating alcohols will be most successful with alcohol groups that are primary and unhindered; tertiary alcohols or otherwise highly hindered alcohols are unlikely to react effectively.

Example 3

Preparation of a Precursor Polymer for a Vinylically-Bound Drug Delivery Composition Incorporating a Carbamate Masked Nitrogen Triggering Atom This preparation is illustrated in Scheme 9: To a solution of 4-amino-3-bromophenol (22.5 g) in dry THF (100 mL) under a nitrogen atmosphere is added di-tert-butyldicarbonate (34 g). After stirring for 30 minutes, the solution is heated at reflux for 18 hours. After removal of solvent by rotary evaporation, the Boc-derivative is separated from residual 4-amino-3-bromophenol by chromatography on silica gel. A portion of the 4-tert-butoxycarbonylamido-3-bromophenol so obtained (23 g) is dissolved in peroxide free THF (200 mL) and tetrabutylammonium hydroxide added (50 mL of a 40% by weight solution). The resulting mixture is rapidly stirred for 15 minutes, then combined with poly(vinylbenzyl chloride) (3 g) and the mixture shaken for twelve hours. The polymer is then washed with ethanol and dichloromethane to remove excess reagents, and finally with dry ether. The polymer is then dried under high vacuum and weighed to provide an estimate of the incorporation of Boc-protected bromide. Dry THF (60 mL) is added to the polymeric Boc-protected bromide and the mixture cooled under nitrogen to −78° C. To the swirled mixture is slowly added 2.2 molar equivalents of n-BuLi (as a roughly 2.5 M solution in hexanes). Swirling is continued for 20-30 minutes after completion of the addition, and then 1.1 molar equivalents of freshly distilled 2-propynal (propargyl aldehyde) is added. After an additional 1 hour reaction time with swirling at −78° C. the reaction is quenched by addition of saturated aqueous ammonium chloride (5 mL) and allowed to warm to room temperature. The polymer is centrifuged, the supernatant removed, and then washed with cold ethanol, followed by dichlomethane to remove the ethanol. The polymeric propargyl alcohol is then weighed to provide an estimate of the yield. The polymeric propargyl alcohol is combined with dichloromethane and four molar equivalents of 2,6-di-tert-butylpyridine. Freshly purified Dess-Martin periodinane reagent (1,1,1-triacetoxy-1,1-dihydro-1,2-benziodoxol-3(1H)-one, 1.5 molar equivalents) is added and the mixture swirled for four hours at room temperature. The resulting precursor polymeric delivery composition is centrifuged, the supernatant removed, and the solid washed with methanol to remove residual oxidant.

Example 4

Preparation of a Polymeric Vinylically-Bound Fentanyl Delivery Composition Having an Amine Nucleophilic Triggering Atom This preparation is illustrated in Scheme 10. A saturated methanol solution of the tetrafluoroborate salt of fentanyl is combined with the polymeric precursor for the drug delivery composition incorporating a carbamate masked nitrogen triggering atom, along with sufficient methanol to cover the polymer, and the mixture heated at reflux until the reaction is complete. Excess fentanyl is recovered by centrifugation or filtration, and the resin is washed with methanol to complete this recovery. Those familiar with the art recognize that different drugs may require somewhat different conditions to accomplish the conjugate addition reaction to the alkynyl group of the delivery precursor. The use of alternative polar solvents may be desirable (e.g., DMF, nitromethane, or in

SCHEME 9

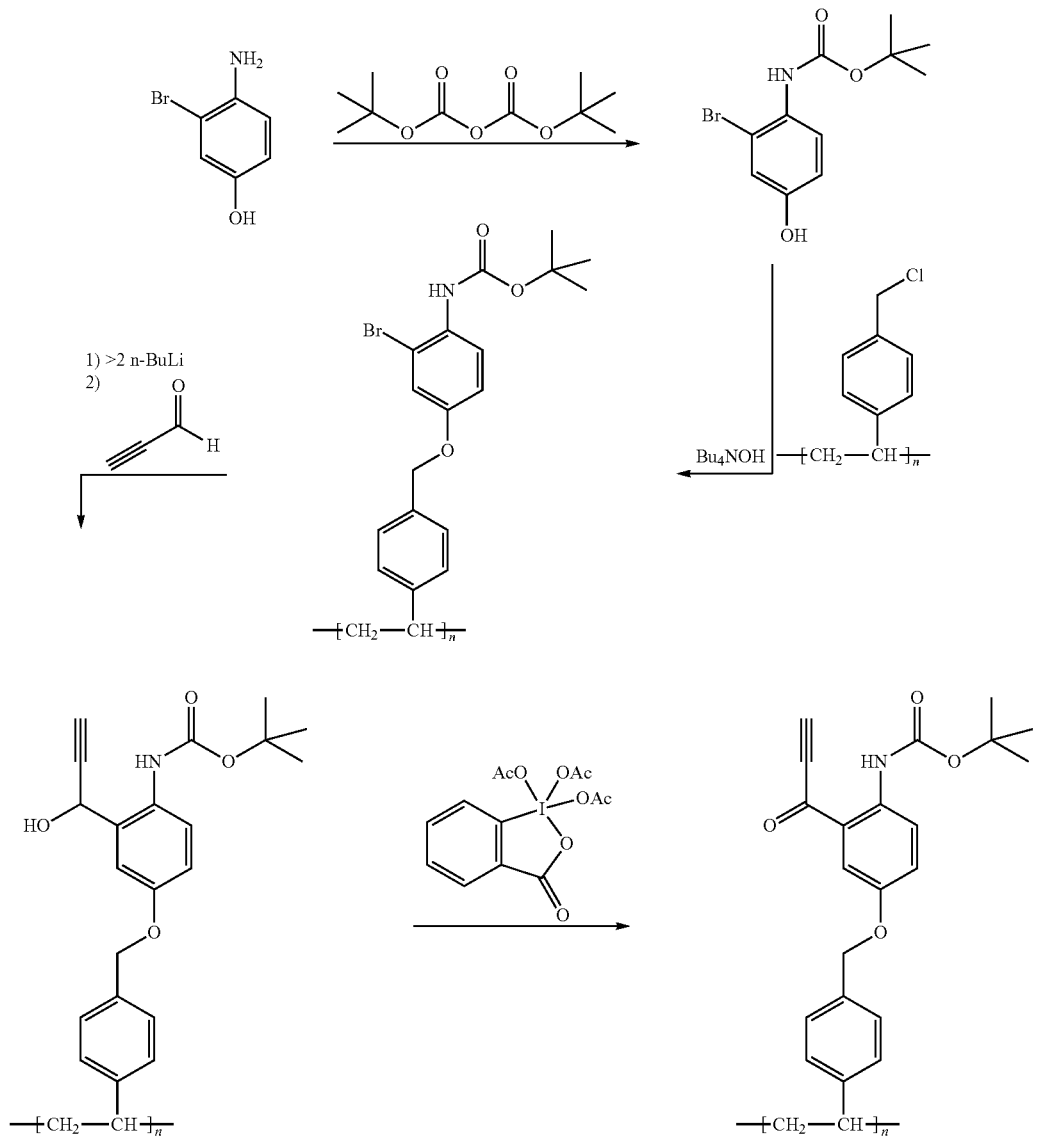

some cases higher boiling alcohol solvents), as may be the use of more elevated temperatures may be employed, provided that conditions are chosen such that loss of the masking group does not occur (e.g., no acidic substrates or solvents). The use of high pressure (>5 kbar) may also facilitate the reaction. It is also clear to those familiar with the art that drugs incorporating secondary amines and primary amines will generally react with greater ease to form the corresponding drug delivery composition, and that it may not be necessary to utilize the fluoroborate salt of the amine. It is also clear that drugs incorporating an alcohol or thiol will react with the drug delivery composition precursor, preferably in the presence of a catalytic amount of a hindered or otherwise non-nucleophilic base, to give the corresponding drug delivery composition. Reactions of drugs incorporating alcohols will be most successful with alcohol groups that are primary and unhindered; tertiary alcohols or otherwise highly hindered alcohols are unlikely to react effectively.

SCHEME 10

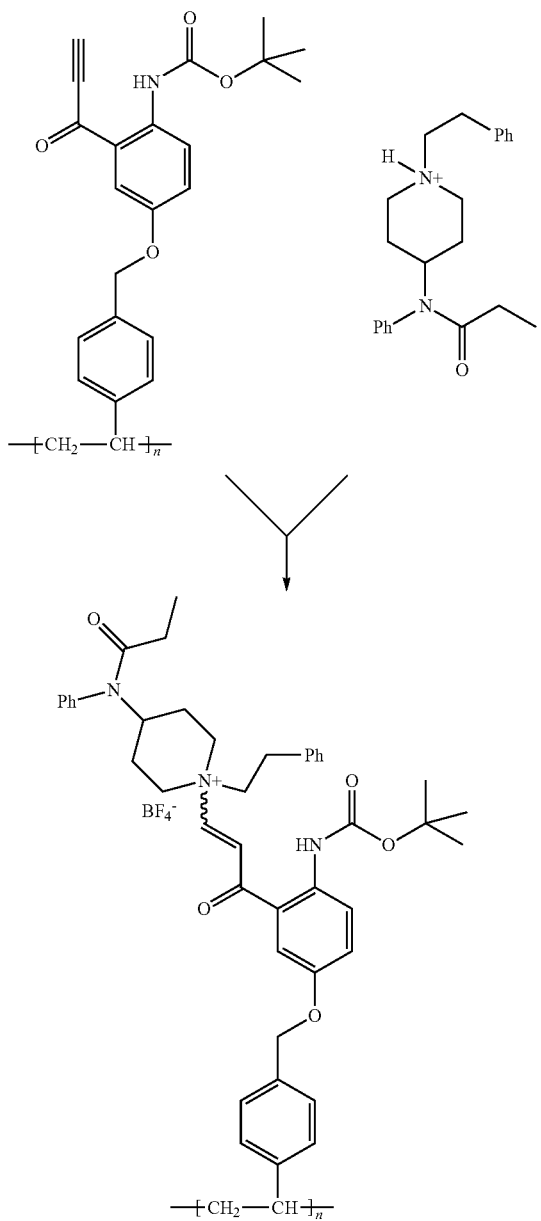

Operation of the Polymeric Vinylically-bound Drug Delivery Composition.

The polymeric fentanyl drug delivery composition may be encapsulated or put into tabular form. If chewed in the mouth, no fentanyl will be released, since quaternary vinylammonium salts are quite stable in neutral aqueous solution, and the masking ethoxyethyl group (or tert-butoxycarbonyl group) is stable to neutral and basic aqueous conditions (e.g., stable to pH>4). However, when swallowed, the ethoxyethyl masking group (i.e., the alcohol protecting group), or the tert-butoxycarbonyl group (i.e., the amine protecting group) will be hydrolyzed rapidly in the strongly acidic environment of the stomach. This will unmask the triggering group, which will then engage in an intramolecular nucleophilic substitution reaction by an addition-elimination sequence to release fentanyl in its physiologically active form.

Example 5

Preparation of a Precursor Polymeric Fragmentation-Based Drug Delivery Composition Having an Amine Donor Atom with a Simple Masking Group This procedure is illustrated in Scheme 11. Poly(vinylbenzoic acid) (2.95 g) is combined with thionyl chloride (10 mL) in a 50 mL flask equipped with a condenser. The mixture is gently refluxed for four hours, allowed to cool, and the condenser replaced by a distilling head. Excess thionyl chloride is distilled out under moderate vacuum (15-50 ton), taking care that moisture cannot enter the system. To remove residual thionyl chloride, dry carbon tetrachloride (10 mL) is added, the mixture swirled throughly, and the liquid distilled out under vacuum. This washing procedure is repeated an additional two times. The resulting poly(vinylbenzoyl chloride) is combined with dry tetrahydrofuran (THF, 20 mL), cooled under nitrogen in ice/water for thirty minutes with occasional swirling, and 2-(2-aminoethyl)ethanol (16 mL) is added dropwise with gentle swirling at a rate such that the temperature of the mixture does not rise above 10° C. When addition is complete the mixture is allowed to stand for an additional thirty minutes, and then the flask is transferred to an orbital shaker and swirled for twelve hours. Methanol (100 mL) is then added and swirling continued an additional twelve hours. The mixture is then transferred to a series of centrifuge tubes, centrifuged, and the supernatant solution removed. The polymer is then washed successively with methanol, ethanol and water to remove excess amine and chloride salt. The polymer is then washed with ethanol to remove water, dried under vacuum, and then washed with dry THF to remove remaining traces of ethanol (some ethanol may remain, but will react with p-toluenesulfonyl chloride in the following step, potentially decreasing the yield). After drying under high vacuum the polymer is weighed to determine a rough yield.

The poly(vinylbenzoic amide) of 2-(2-aminoethyl)ethanol so obtained is combined with dry THF (50 mL), 2,6-lutidine (10 mL) and cooled in ice with occasional swirling, protecting at all times against moisture. Freshly crystallized p-toluenesulfonyl chloride (p-TsCl, 15 g) is added in portions to the cold mixture with occasional swirling, and then the mixture is swirled with an orbital shaker for 12 hours at 0° C. The reaction mixture is then transferred to centrifuge tubes, centrifuged, and the supernatant removed. The resulting polymeric tosylate is washed with sufficient cold ethanol and then cold dichloromethane to remove excess lutidine and p-TsCl, dried under vacuum, and weighed to determine a rough yield.

The polymeric tosylate is added to a cold solution of ethyl p-aminobenzoate (19.8 g) in ethanol free chloroform (90 mL), and the mixture swirled on an orbital shaker for 12 hours. Centrifugation and removal of the supernatant is followed by washing with ethanol and then dichloromethane to remove excess ethyl p-aminobenzoate, to give the ethyl ester of the aminobenzoate polymer. This polymer is then dried under high vacuum, weighed, and then combined with a solution of di-tert-butyldicarbonate (27 mL) in ethanol free chloroform (25 mL). After swirling for two hours at room temperature, the mixture is heated to reflux for 18 hours. After cooling to room temperature, the mixture is centrifuged, washed with chloroform to remove excess di-tert-butyldicarbonate, dried under vacuum, and weighed to provide an estimate of the amount of polymeric Boc-protected ester.

The polymeric Boc-protected ester is combined with methanol (100 mL), water (10 mL) and tetrabutylammonium hydroxide (an amount corresponding to 2-3 molar equivalents of the ester, as estimated by the weight of the polymer). The mixture is swirled at 35-40° C. for approximately 6 hours. The polymer is centrifuged, the supernatant removed, and then the polymer is washed with several portions of 0.1 M acetic acid in 50% methanol/water, 0.1 M acetic acid in methanol, and then methanol to remove excess acetic acid. After drying under vacuum to remove the bulk of residual methanol, the polymer is washed with two portions of dry THF, and then combined with cold borane-THF solution (60 mL of a 1 M solution) and swirled for four hours. Centrifugation and removal of that supernatant is followed by resuspension in THF and cautious addition of methanol to quench residual borane. The polymer is then washed with 0.1 M acetic acid in methanol to remove borate salts, methanol, dichloromethane and then dried and weighed.

The polymeric Boc-protected benzylic alcohol may be converted to either the corresponding bromide or tosylate to make an active resin suitable for coupling to an alcohol, amine or thiol containing drug. Of course, other active resins could also be prepared (e.g., iodide, mesylate, other sulfonate or sulfate). To prepare the bromide activated resin, the polymeric Boc-protected benzylic alcohol is combined with dichloromethane (100 mL) and carbon tetrabromide (26 g), the mixture cooled to 0° C., and then triphenylphosphine (21 g) is slowly added and the reaction swirled for an hour at 0°. The mixture is then centrifuged, the supernatant removed, and the polymer washed with dichloromethane to remove triphenylphosphine, carbon tetrabromide and reaction byproducts.

Alternatively, the polymeric Boc-protected benzylic alcohol is combined with ethanol free chloroform (50 mL) and dry 2,6-lutidine (10 mL), the mixture cooled to −5° C., and p-TsCl (15 g) is added. The mixture is swirled on an orbital shaker at −10° to 0° for 24 hours, then centrifuged cold, the supernatant removed, and then the polymeric Boc-protected tosylate washed with cold ethanol free chloroform to remove excess lutidine and p-TsCl. The polymer is dried under vacuum while cold, then weighed to obtain an estimated yield. The polymer should be stored in the cold, and reacted soon with the target drug.

SCHEME 11

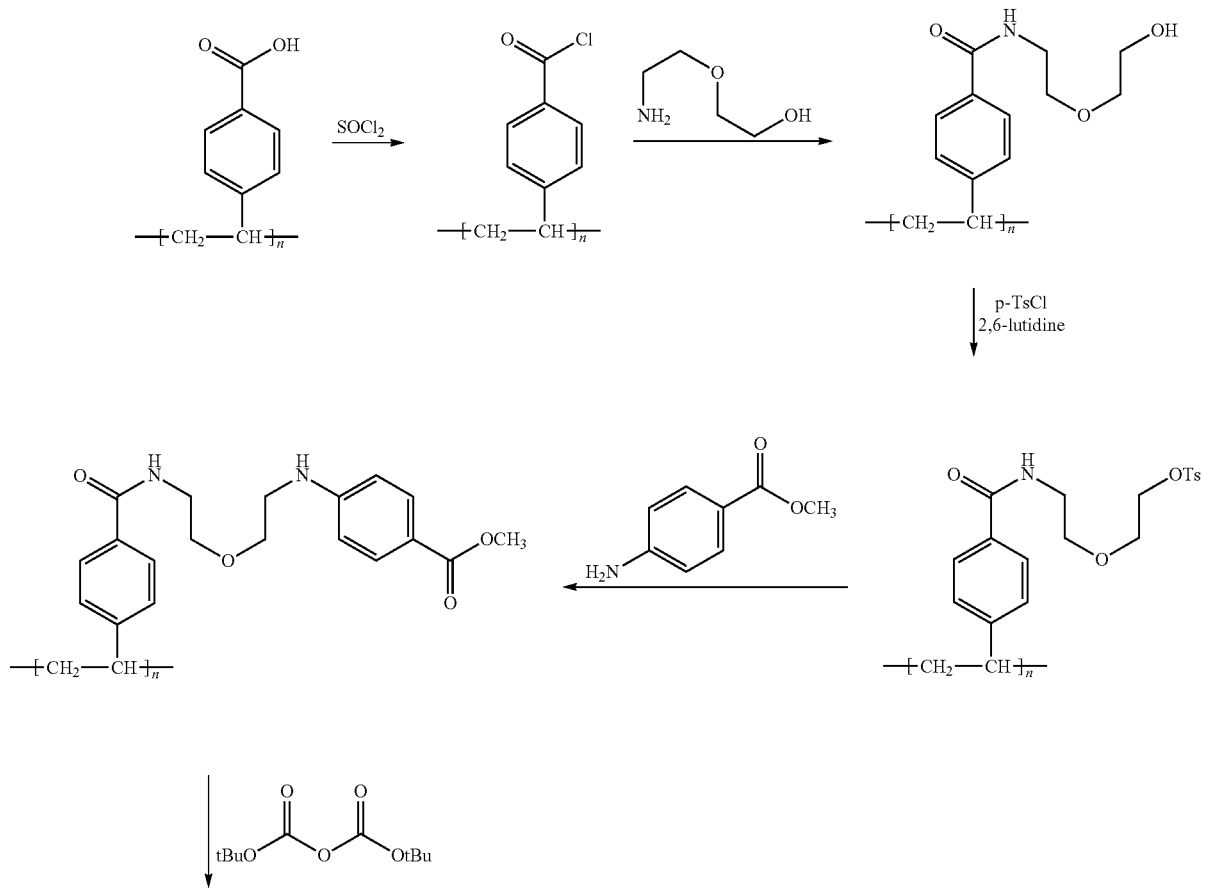

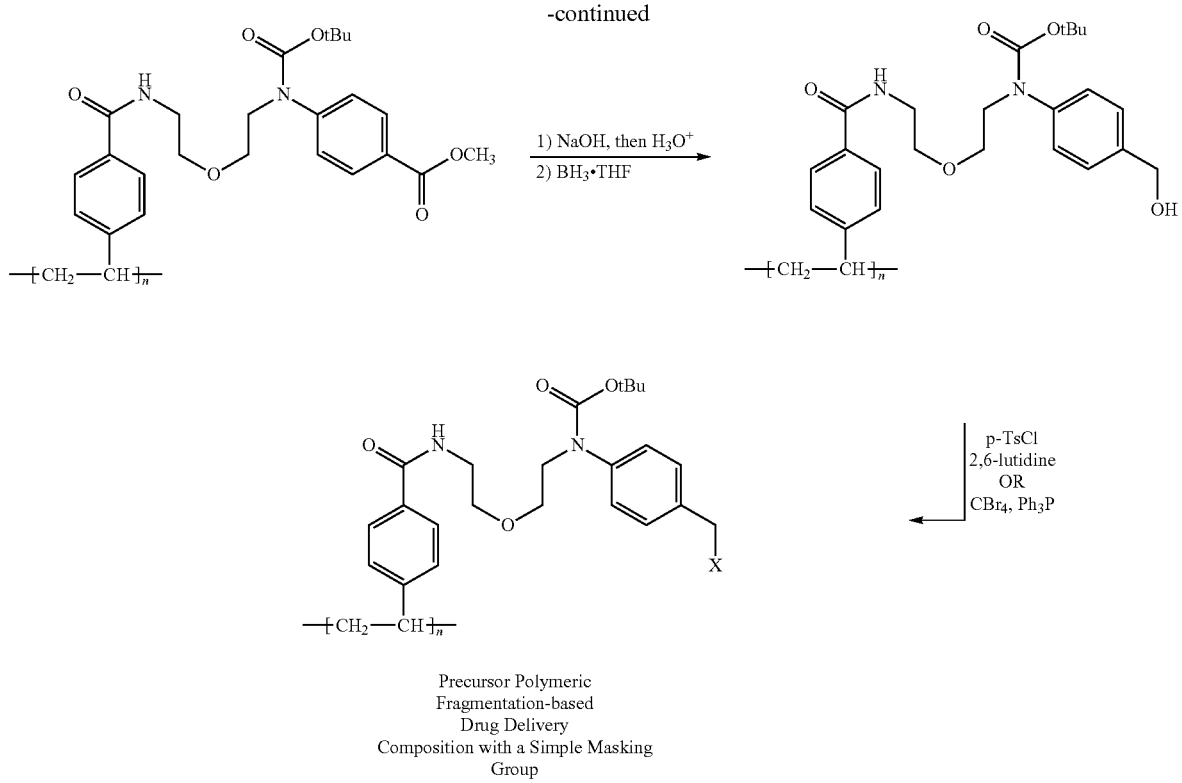

Precursor Polymeric
Fragmentation-based
Drug Delivery
Composition with a Simple Masking
Group Example 6

Preparation of a Polymeric Fragmentation-Based Oxycodone Delivery Composition Having an Amine Donor Atom with a Simple Masking Group This preparation is illustrated in Scheme 12. The polymeric Boc-protected tosylate prepared as described above is covered with a saturated solution of oxycodone in ethanol free chloroform and allowed to stand at room temperature for 24 hours. The amount of unreacted oxycodone is monitored over time by periodic removal of aliquots and assay by an appropriate technique (HPLC is convenient) for the presence of oxycodone; if all of the oxycodone disappears, additional portions of oxycodone saturated chloroform are added. In the monitoring of the reaction it is, of course, important to distinguish between physical adsorption onto the polymer matrix an true covalent binding; this may be determined by thoroughly washing an aliquot of the polymer with a known amount of solvent and determining the amount of oxycodone removed by standard analytical techniques. When it is judged that the reaction with oxycodone is complete, the resin is washed with chloroform to recover excess oxycodone, which may then be recovered. In order to ensure that no reactive tosylates remain in the resin, it is combined with ten volumes of methanol and at least one molar equivalent of diisopropylethylamine relative to the calculated amount of tosylate originally contained in the resin. The mixture is then swirled for four to six hours and washed with methanol to remove all traces of diisopropylethylamine. This latter treatment results in the conversion of any remaining benzyl tosylate groups to methyl benzyl ethers.

It should be clear to one familiar with the art that the preceding invention can be modified in a number of ways without substantial change. For example, the rate at which drug is delivered from the device can be modified by use of different carbamate protecting groups having different sensitivities to acid. The level of oxycodone incorporation onto the polymer may be modified by the use of different solvents (e.g., nitromethane, formamide based solvents), provided however, that the solvent used will not react with the tosylate (e.g., alcohol solvents). In place of a tertiary amine drug, such as the oxycodone described above, secondary and primary amine drugs can be attached to the polymer in much the same way as oxycodone. For preparation of controlled release devices for drugs that incorporate an alcohol moiety, a chloroform solution of the drug is combined with slightly more than one equivalent of a hindered base (diisopropylethylamine is convenient) and swirled with the Boc-protected bromide or tosylate on an orbital shaker until the reaction is complete. One familiar with the art knows that drugs incorporating primary alcohol moieties will react more rapidly than those having secondary alcohols, and that drugs incorporating tertiary alcohols will react with difficulty, if at all. The procedure for preparing controlled release devices for drugs incorporating a thiol moiety is similar to that for drugs incorporating an alcohol moiety; however, it is especially important for this class of compounds that oxygen free conditions are employed, to avoid the formation of disulfides.

Example 7

Preparation of a Precursor Polymeric Fragmentation-Based Drug Delivery Composition Having an Amine Donor Atom with a Two-Stage Masking Group Triethylamine (10 mL) is combined with 5-amino-pentanoic acid (9.4 g) in a 20% THF/water mixture (100 mL) and the mixture rapidly stirred for one hour. Di-tert-butyldicarbonate (22 g) is added and the mixture stirred rapidly for eight hours. The bulk of the THF is removed with a rotary evaporator, and the mixture extracted with diethyl ether (3×25 mL). The remaining aqueous is cooled to 0° C. and carefully, but rapidly acidified to pH 5. The resultant mixture is extracted with ice-cold chloroform (3×40 mL), the chloroform extracts dried with sodium sulfate, and the drying agent filtered off, to provide a chloroform solution of the Boc-protected pentanoic acid. To this dry solution is added carbonyl diimidazole (9.7 g), followed fifteen minutes later by N-hydroxybenzotriazole (8 g). After stirring for approximately one hour, the solution is applied to the ethyl ester of the aminobenzoate polymer prepared as described above for the controlled release device employing a single masking group; the resulting mixture is swirled with an orbital shaker for eight hours. The resulting polymer is washed with chloroform to remove excess reagents, dried under high vacuum, and weighed. The remainder of the sequence to convert this polymer to the controlled delivery device having a two stage masking group is the same as described as for the controlled delivery device having a single masking group; i.e., hydrolysis of the ester, conversion to the acid, reduction with borane, and final conversion to either the tosylate or bromide.

SCHEME 12

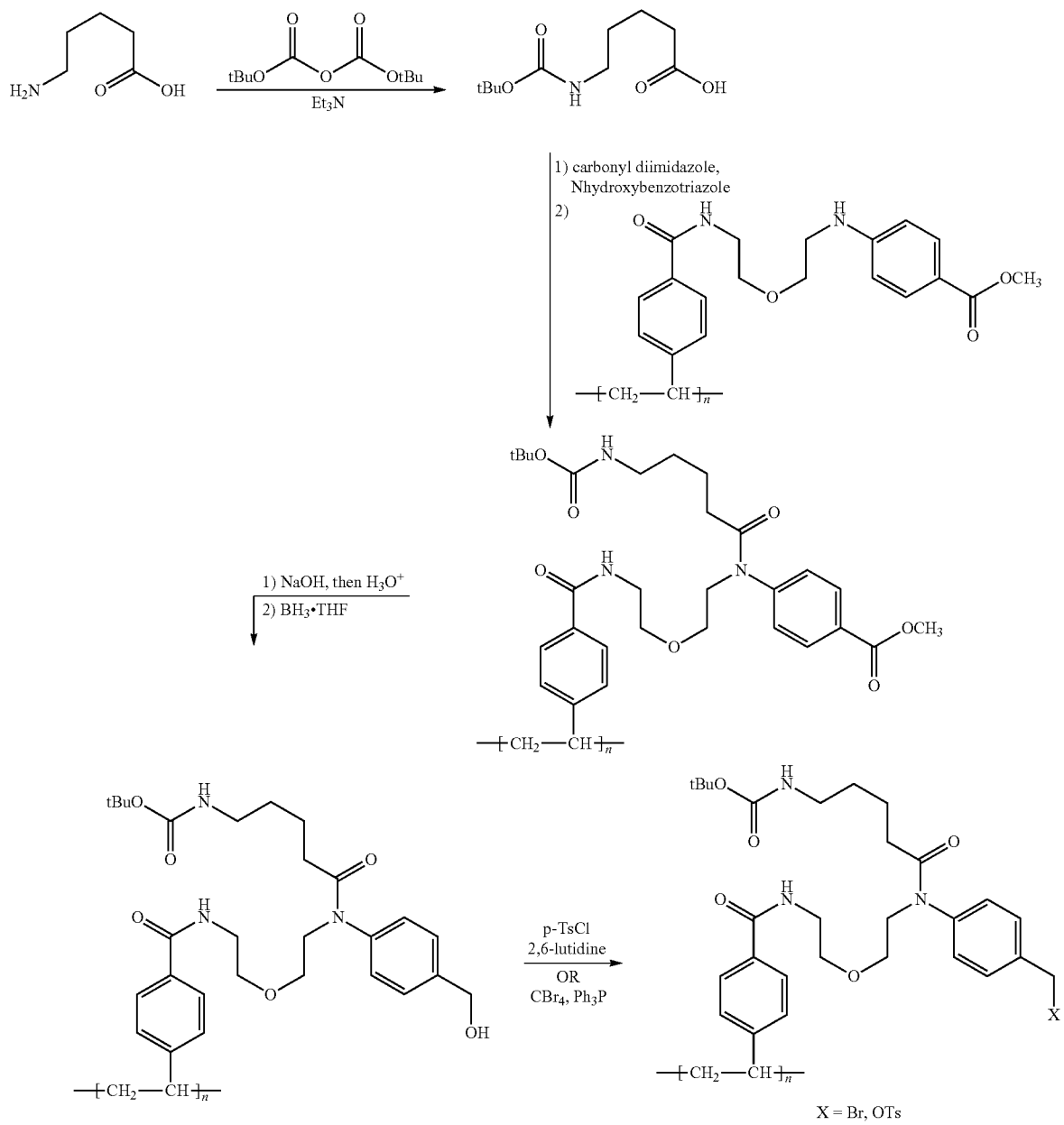

Precursor Polymeric Fragmentation
Based Drug Delivery Composition
Having a 2-Stage Masking Group Formation of drug delivery compositions from the 2-stage fragmentation precursor-proceeds similarly to those from the simple masking group compositions. The same considerations with respect to the range of drugs amenable to use with this composition also apply.

Example 8

Preparation of a Precursor Polymeric Elimination-Based Drug Delivery Composition Having a Single Masked Electron Withdrawing Group This preparation is illustrated in Scheme 13. Poly(vinylbenzoyl chloride) is combined with 4-5 volumes of ethanol-free chloroform and cooled under nitrogen atmosphere to 0° C. While gently swirling the mixture, six molar equivalents of N-methyl-4-aminobutanol are added. The mixture is swirled on an orbital shaker for 12 hours, and then excess solvent/reagent removed by centrifugation and washing with ethanol, and then methylene chloride. The polymeric alcohol is then dried under vacuum and weighed to determine the yield of the amide. This yield may also be inferred by analyzing the combined supernatant and washes for the amount of unreacted-methyl-4-aminobutanol. The polymer is covered with four volumes of dry dichloromethane, and 2 molar equivalents of Dess-Martin periodinane are added. After swirling six hours the solvent and excess reagent are removed by centrifugation and washing with dichloromethane. The resulting polymeric aldehyde is dried under vacuum and weighed to obtain an estimate of the yield; it should be used without substantial delay in the next reaction. The polymeric aldehyde is covered with 4-5 volumes dry THF and cooled to roughly −78° C. under nitrogen with swirling. Slightly less than one molar equivalent of a solution of vinyl lithium is added to the swirled solution. The mixture is swirled at this temperature for an additional hour, and then the reaction is quenched by addition of saturated aqueous ammonium chloride. After allowing the mixture to warm to room temperature, salts are removed by washing with methanol, the methanol is washed out with several portions of dichloromethane, and the polymeric allylic alcohol dried and weighed to obtain a yield estimate. The polymeric allylic alcohol is covered with four volumes of dry dichloromethane and 2 molar equivalents of Dess-Martin periodinane are added. After swirling six hours, the solvent and excess reagent are removed by centrifugation and washing with dichloromethane. After drying under high vacuum, the polymer is weighed to obtain an estimate of the yield of polymeric enone.

The polymeric enone is converted to the precursor polymeric elimination-based drug delivery device in a manner similar to that of Stowell et al. (*Organic Syntheses, Collective Volume VII*, page 58) used for methyl vinyl ketone. Thus, the polymer is covered with roughly 10 volumes dry dichloromethane, a small portion of dicinnamalacetone pH indicator added, and anhydrous hydrogen bromide bubbled into the solution until a persistent red color is obtained. Because of the slower kinetics of reaction for the polymeric enone, it is important to stop HBr addition after a red color appears, but continue swirling to see if the color persists; if it does not, then more HBr should introduced. After a persistent color change is observed, 2 molar equivalents each of 2,2-dimethyl-1,3-propanediol and triethylorthoformate are added, along with 0.01 molar equivalent p-toluenesulfonic acid. The mixture is swirled with an orbital shaker for six hours, and then the precursor polymeric elimination-based drug delivery composition incorporating a masked electron withdrawing group is freed of excess reagent and acid by washing with dichloromethane.

Example 9

Preparation of a Polymeric Elimination-Based Oxycodone Delivery Composition Incorporating a Masked Electron Withdrawing Group The precursor delivery composition of Example 8 is combined with 0.1 molar equivalents of tert-butylammonium iodide and with a DMF solution of oxycodone and the mixture heated. The progress of the reaction can be monitored by removing aliquots of the supernatant and assaying for either bromide appearance or oxycodone loss. After the desired level of incorporation has been achieved any excess oxycodone is recovered by centrifugation and washing with methanol. Any excess active bromide sites may be removed by adding 6-10 volumes 5% trimethylamine in methanol and swirling for several hours. The resulting delivery composition is then washed again with methanol to remove traces of trimethylamine and dried under high vacuum.

SCHEME 13

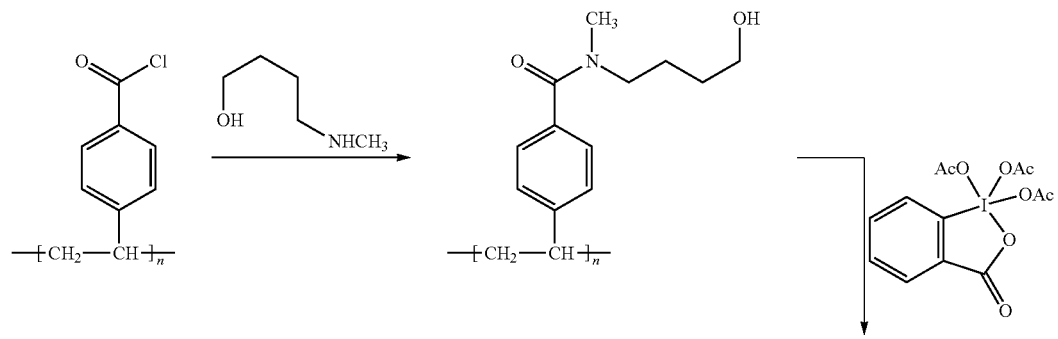

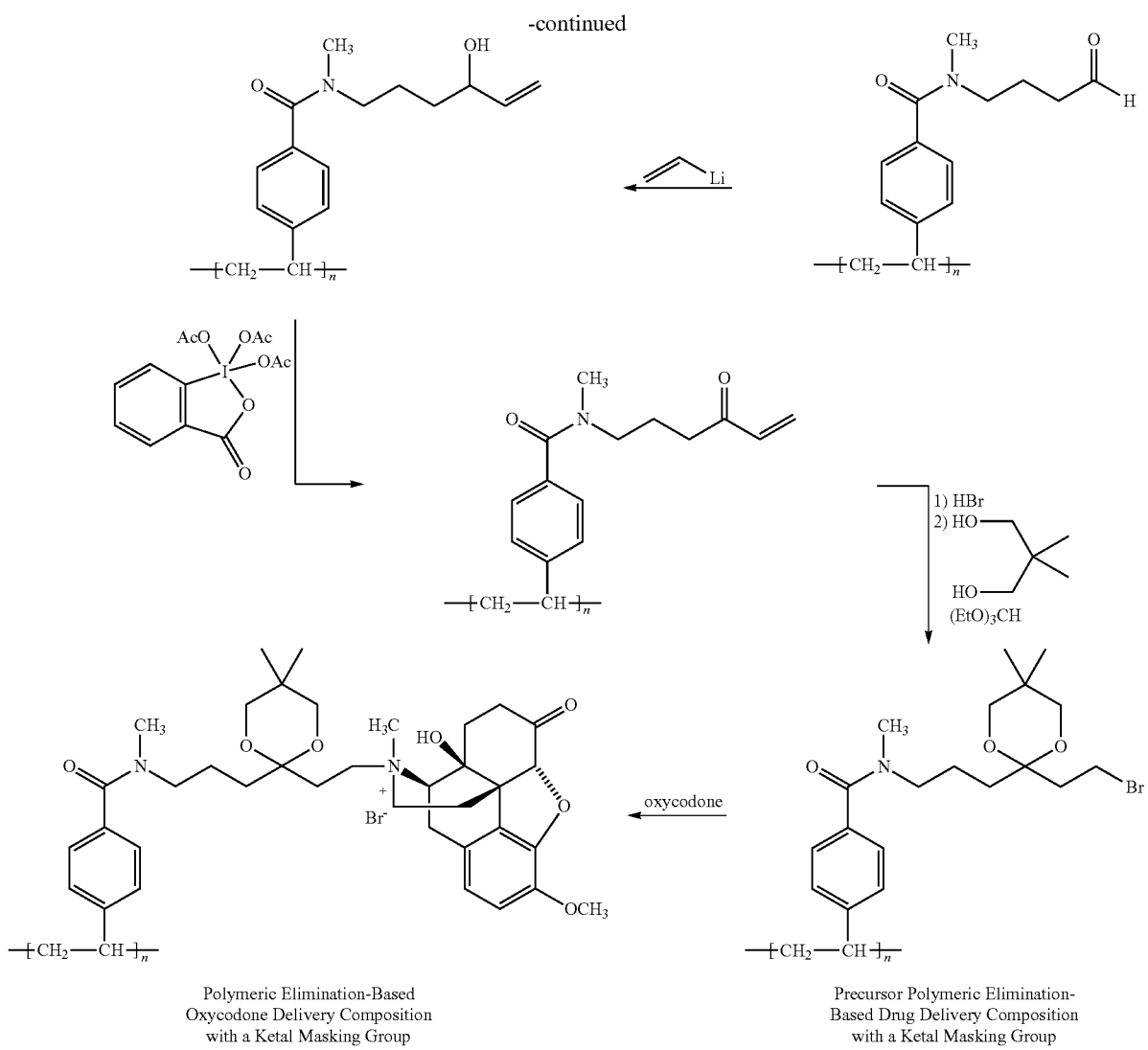

Polymeric Elimination-Based
Oxycodone Delivery Composition
with a Ketal Masking Group Precursor Polymeric Elimination-
Based Drug Delivery Composition
with a Ketal Masking Group It is obvious to one familiar with the art that any of a number of tertiary amine drugs could be similarly reacted with the precursor polymer to give the corresponding controlled release devices. The precursor polymer can also be reacted with secondary amines, and this reaction will in most cases take place more readily than that of tertiary amine drugs. Drugs incorporating primary amines may also react, but it may be desirable to utilize a precursor polymer that does not have a high loading capacity; that is, a polymer in which incorporation of the alkyl bromide units is not at a high level. This may be desirable to avoid the possibility of two of the alkyl bromides reacting with the primary amino group of the drug. This precursor polymeric delivery system may also be employed with drugs incorporating alcohols, though most advantageously with phenolic drugs. Phenolic drugs are preferred for this device because of their superior leaving group ability relative to aliphatic alcohols, although there may also be aliphatic alcohols that, by reason of some special structural characteristic(s) may be effectively used with this device. In this case, the polymeric drug delivery composition will be formed by reaction of the phenolic (or alcoholic) drug with the precursor polymer in the presence of a base.

Example 10

Preparation of a Precursor Polymeric
Enamine-Based Controlled Release Drug
Composition This preparation is illustrated in Scheme 14. The tert-butoxycarboxamide derivative of 3-prolinol (19 g) is dissolved in dry DMF (200 mL) and sodium hydride (2.5 g) is added in portions over a period of approximately one hour to the stirred solution. Stirring is continued for an additional thirty minutes after visible hydrogen evolution has ended, and then cooled to roughly 0° C. To this mixture, the polymeric tosylate described in Example 5 is added, and the mixture swirled for 4-6 hours at 0°, and then an additional 4-6 hours at room temperature. The polymer is washed with methanol to remove excess reagent and salts, and then treated with p-toluenesulfonic acid in THF/dichloromethane (cf. Brinkman, H. R.; Landi, J. J.; Paterson, J. B.; Stone, P. J., *Synthetic Communications*, 21, 459 (1991)). The polymer is then washed with 1 M NaOMe in methanol, followed by methanol to neutrality. Drying under high vacuum provides the precursor polymeric enamine-based drug delivery composition.

Scheme 14

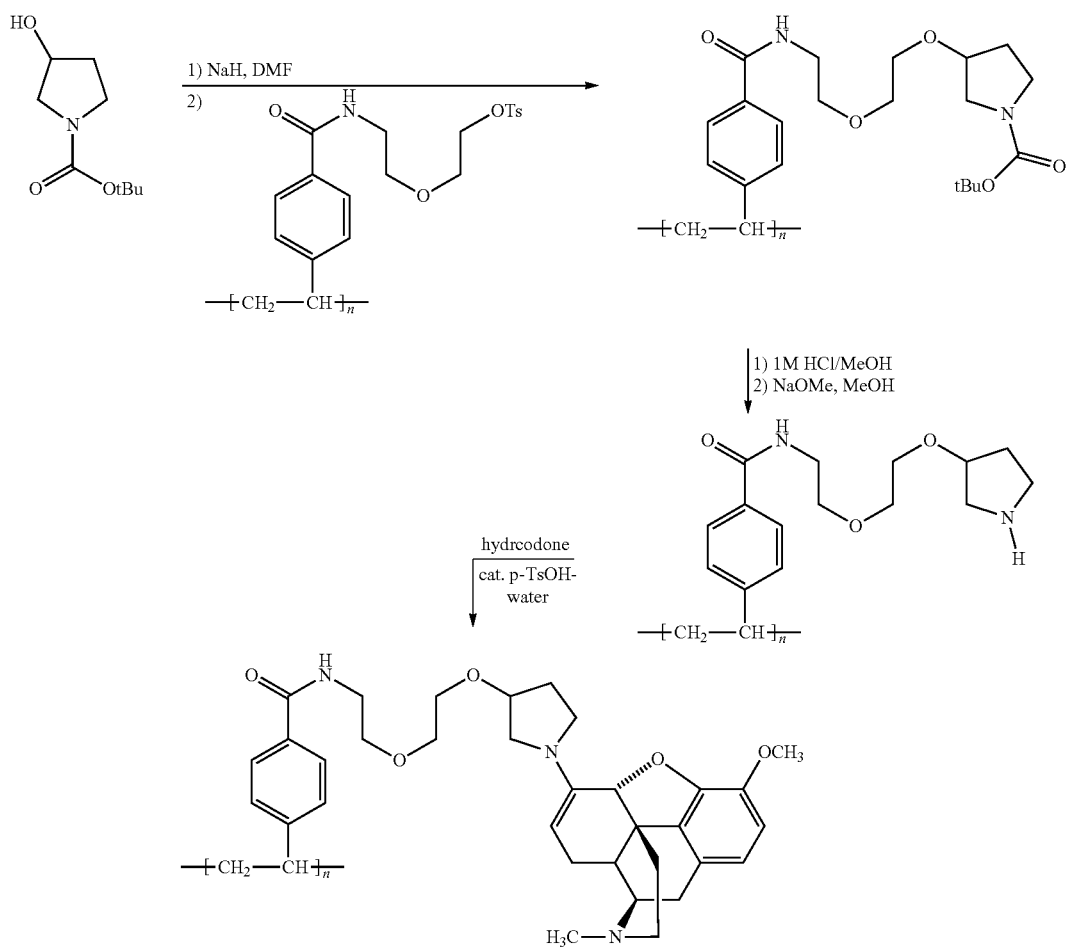

Example 11

Preparation of a Polymeric Enamine-Based Hydrocodone Delivery Composition

Hydrocodone (~3 g) is dissolved in dry toluene (50 mL) and added to the precursor polymeric enamine-based drug delivery composition. p-Toluenesulfonic acid (~0.1 g) is added, a Dean-Stark trap is attached to the flask and the mixture heated to reflux. The extent of reaction may be monitored by examination of the amount of water collecting in the Dean-Stark trap. When no further reaction is evident, the mixture is cooled and the polymer is washed with 0.1 M NaOMe in methanol, followed by methanol and drying under high vacuum.

As is known to those familiar with the art, the speed and extent to which the enamine forming reaction proceeds will be increased by the addition of chemical drying agents, which may be present in the solution, or may be in the Dean-Stark trap (e.g., $CaCl_2$ or $CaSO_4$).

Other drugs containing a ketone or aldehyde moiety may be used with this delivery system, but those familiar with the art will recognize that the ease and extent of enamine formation will be dependent on both steric and electronic factors; similarly, these will play a role in the rate of the drug release. Though a single example of an enamine is given here, those familiar with the art will recognize that changing substituents on the nitrogen of the delivery device may play a significant role in the delivery rate. For example, electron withdrawing groups will tend to give a delivery device that provides a slower rate of delivery; use of cyclic enamines will also tend to give slower delivery rates.

Example 12

Preparation of a Degradable Polymer Incorporating Masked Nucleophilic Triggering Atoms This preparation is illustrated in Scheme 15. Poly(aspartic acid) (2.3 g) is combined with dry DMF (15 mL), followed by addition of tert-butylcarbazate (0.3 g) and 1-[3-(dimethylamino)propyl]-3-ethylcarbodiimide methiodide (0.3 g). The mixture is shaken for 24 hours, then centrifuged, the supernatant removed, and the degradable polymer washed with ethanol and water to remove unreacted reagent(s) and side products.

One familiar with the art will recognize that the rate of polymer degradation will depend on the degree of incorporation of the masked nucleophilic triggering atoms into the polymer, with a greater degree of incorporation leading to more rapid degradation in the intestinal tract. The rate of polymer degradation may also be modified by utilization of other spacer lengths between the nucleophilic nitrogen and the amide linkage in the polymer (e.g., poly(glutaric acid) derived degradable polymers will degrade more slowly, while poly(malonic acid) derived polymers will degrade more rapidly). It is also clear that carbamates that are more, or less susceptible to acidic cleavage may be used to mask the nucleophilic nitrogen. The degree of incorporation of the tert-butyl carbazate into the polymer will of course be dependent on the water content of the solvents and reagents employed.

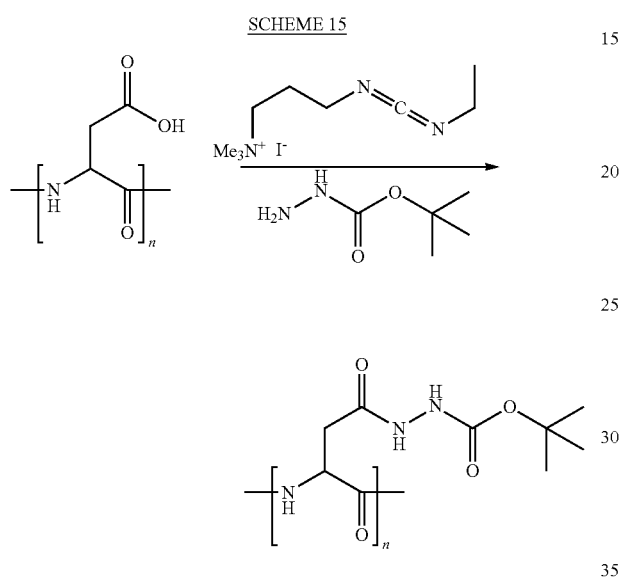

This invention has been illustrated by a number of specific embodiments. However, it will be apparent to those skilled in the art that other drugs, masking groups, triggering groups, polymers, reagent and reaction conditions are equivalent or analogous to those described herein and can be used as appropriate in the practice of this invention. All such equivalents are intended to be encompassed within the scope of the claims hereof.

The invention claimed is:

1. A method for controlled delivery of a drug to a patient comprising administering to the patient a drug-delivery molecule, wherein the drug delivery molecule has the structure:

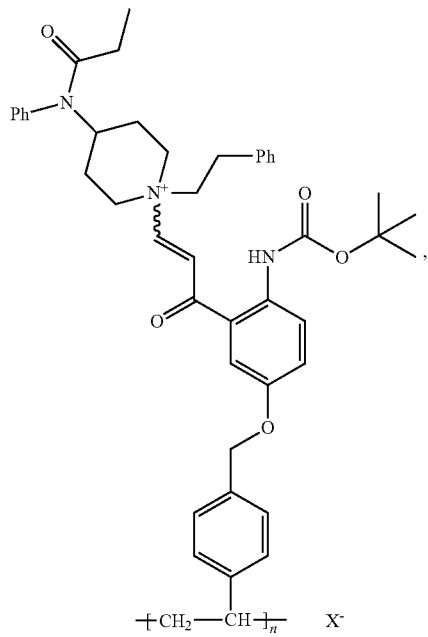

where n is about 10 to about 10,000, and wherein $X^-$ is a counter ion of a pharmaceutical salt.

2. A method for controlled delivery of a drug to a patient comprising administering to the patient a drug-delivery molecule, wherein the drug delivery molecule has the structure:

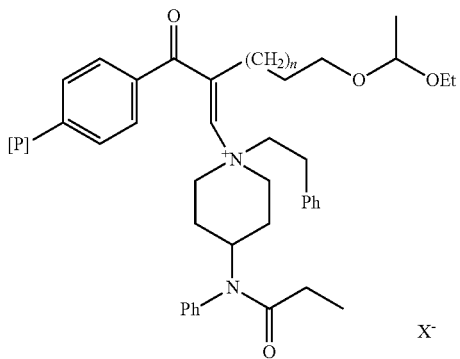

wherein [P] is a pharmaceutically acceptable polymeric moiety; wherein n is 0-2; and
wherein $X^-$ is a counter ion of a pharmaceutical salt.

* * * * *